United States Patent
Schmidt

(10) Patent No.: US 11,651,863 B2
(45) Date of Patent: May 16, 2023

(54) PREDICTING PROSTATE CANCER RECURRENCE USING A PROGNOSTIC MODEL THAT COMBINES IMMUNOHISTOCHEMICAL STAINING AND GENE EXPRESSION PROFILING

(71) Applicant: AstraZeneca Computational Pathology GmbH, Munich (DE)

(72) Inventor: Guenter Schmidt, Munich (DE)

(73) Assignee: AstraZeneca Computational Pathology GmbH, Munich (DE)

( * ) Notice: Subject to any disclaimer, the term of this patent is extended or adjusted under 35 U.S.C. 154(b) by 1090 days.

(21) Appl. No.: 16/271,827

(22) Filed: Feb. 9, 2019

(65) Prior Publication Data
US 2019/0252044 A1 Aug. 15, 2019

Related U.S. Application Data

(60) Provisional application No. 62/629,591, filed on Feb. 12, 2018.

(51) Int. Cl.
| | |
|---|---|
| *G16H 50/30* | (2018.01) |
| *G16B 25/10* | (2019.01) |
| *G16B 45/00* | (2019.01) |
| *G16B 20/00* | (2019.01) |
| *G16B 40/00* | (2019.01) |
| *G16H 40/63* | (2018.01) |
| *G01N 33/574* | (2006.01) |
| *G16H 30/40* | (2018.01) |
| *G16H 50/20* | (2018.01) |
| *G16B 40/20* | (2019.01) |
| *C12Q 1/6886* | (2018.01) |

(52) U.S. Cl.
CPC .......... *G16H 50/30* (2018.01); *C12Q 1/6886* (2013.01); *G01N 33/57434* (2013.01); *G16B 20/00* (2019.02); *G16B 25/10* (2019.02); *G16B 40/00* (2019.02); *G16B 40/20* (2019.02); *G16B 45/00* (2019.02); *G16H 30/40* (2018.01); *G16H 40/63* (2018.01); *G16H 50/20* (2018.01); *G01N 2570/00* (2013.01); *G01N 2800/342* (2013.01); *G01N 2800/52* (2013.01); *G01N 2800/54* (2013.01); *G01N 2800/7028* (2013.01)

(58) Field of Classification Search
None
See application file for complete search history.

(56) References Cited

U.S. PATENT DOCUMENTS

2017/0365053 A1  12/2017  Yuan .................. G06T 7/12

OTHER PUBLICATIONS

Schoenber et al. Frozen Tumor Tissue Microarray Technology for Analysis of Tumor RNA, DNA, and Proteins American Journal of Pathology, vol. 159, No. 5, Nov. 2001.*
Pike et al. A Minimum Spanning Forest-Based Method for Noninvasive Cancer Detection With Hyperspectral Imaging IEEE Transactions on Biomedical Engineering, vol. 63, No. 3, Mar. 2016.*
McNeilly et al. A comparison of in situ hybridization and immunohistochemistry for the detection of a new porcine circovirus in formalin-fixed tissues from pigs with post-weaning multisystemic wasting syndrome (PMWS) Journal of Virological Methods 80 (1999) 123-128.*
Levenson et al. Immunohistochemistry and mass spectrometry for highly multiplexed cellular molecular imaging, Laboratory Investigation (2015) 95, 397-405.*
Harder et al., "Combining Immunophenomics with a gene expression panel for improved prostate recurrence prediction," Journal for Immunotherapy of Cancer, vol. 5, No. Suppl. 2, Nov. 7, 2017, p. 2 0f 244 XP055607391 (1 page).
Jia-Mei Chen et al., "Computer-aided prognosis on breast cancer with hematoxilyn and eosin histopathology images," Tumor Biology, vol. Mar. 2017:1-12, Mar. 1, 2017 XP055607422 (13 pages).
Prantik Chatterjee et al.,Journal of Bioinformatics and Computational Biology, vol. 14, No. 1, Feb. 24, Imperial College Press 2016 XP055607117 (20 pages).
Schmidt et al., "Combining immunophenomics with a gene expression panel to deepen the understanding of prostate cancer progression," MMTC Molecular Med Tri-Con conference, Feb. 12, 2018, presentation (15 pages).
Harder, Schmidt et al., "Combining immunophenomics with a gene expression panel for improved prostate cancer recurrence prediction," SITC Society for Immunotherapy of Cancer, Nov. 12, 2017, presentation (20 pages).

* cited by examiner

*Primary Examiner* — Joseph Woitach
(74) *Attorney, Agent, or Firm* — Imperium Patent Works; Darien K. Wallace

(57) ABSTRACT

A method that provides a graphical indication of whether a patient will have cancer recurrence uses univariate and bivariate prognostic features that were generated as part of a minimal spanning tree (MST). The method determines the values of first and second features. A first value is measured by detecting objects in an image of tissue from the cancer patient stained with a protein-specific IHC biomarker. A second value is measured using objects marked with an mRNA-specific probe biomarker detected in the tissue. The first feature is the univariate prognostic feature for cancer recurrence in a cohort of cancer patients. A combination of the first and second features is the bivariate prognostic feature for cancer recurrence in the cohort. The first and second features are elements of the MST. Nodes of the MST represent the univariate features, edges represent the bivariate features, and edge weights represent prognostic significance of bivariate features.

14 Claims, 29 Drawing Sheets

EXTENDED MINIMAL SPANNING TREE (MST) OF UNIVARIATE AND BIVARIATE FEATURES THAT PREDICT PSA RECURRENCE

| |
|---|
| IHC_DIST_CD163(+)_CD8(+)_STROMA |
| IHC_DIST_CD163(+)_CD3(+)CD8(-) |
| IHC_DIST_CD34(+)_CD163(+)_STROMA |
| CD59 |
| MAGEC2 |
| ATF2 |
| NFKBIA |
| CXCL13 |
| NUP107 |
| IL12A |
| JAK2 |
| SYCP1 |
| MAPK1 |
| TBX21 |
| SYK |
| ANXA1 |
| PMCH |
| MBL2 |
| C4B |
| BMI1 |
| CCL5 |
| STAT4 |
| IRF1 |
| CD47 |
| PSEN2 |
| CD96 |
| CTSH |
| IL17B |
| DDX43 |
| KLRK1 |
| LGALS3 |
| PTGDR2 |

- Average distance of CD163(+) cells to CD8(+) cells in stroma
- Average distance of CD163(+) cells to CD3(+)CD8(-) cells on whole slide
- Average distance of CD34(+) cells to CD163(+) cells in stroma

UNIVARIATE FEATURES DETERMINED TO SIGNIFICANTLY PREDICT PSA RECURRENCE

FIG. 5

STARTING DIGITAL IMAGE OF
FIRST TISSUE SLICE (CD68/CD163 STAINED)

STARTING DIGITAL IMAGE OF SECOND
TISSUE SLICE (CD3/CD8 STAINED)

SEGMENTATION AND CLARIFICATION RESULT IMAGE
( → INDICATES A CD163(+) OBJECT )

( → INDICATES A CD3(+)CD8(-) OBJECT )

DETERMINE AVERAGE DISTANCE FROM EACH CD163(+) OBJECT
TO ITS NEAREST FOUR CD3(+)CD8(-) OBJECTS

| PATIENT ID | LGALS3 RAW MEASUREMENTS | KNOWN PSA RECURRENCE ? |
|---|---|---|
| 1 | 2802 | Yes |
| 2 | 2358 | No |
| 3 | 969 | No |
| 4 | 1159 | No |
| 5 | 1791 | No |
| 6 | 2460 | Yes |
| 7 | 1838 | No |
| 8 | 1307 | Yes |
| 9 | 2409 | Yes |
| 10 | 3842 | Yes |
| 11 | 2650 | Yes |
| 12 | 921 | Yes |
| 13 | 1651 | No |
| 14 | 5485 | No |
| 15 | 1513 | No |
| 16 | 1834 | Yes |
| 17 | 1973 | Yes |
| 18 | 2006 | Yes |
| 19 | 1883 | No |
| 20 | 2844 | No |
| 21 | 2652 | Yes |
| 22 | 3021 | Yes |
| 23 | 1104 | No |

LGALS3 RAW DATA SORTED BY PATIENT ID

FIG. 11

| PATIENT ID | LGALS3 RAW MEASUREMENTS | KNOWN PSA RECURRENCE ? |
|---|---|---|
| 12 | 921 | Yes |
| 3 | 969 | No |
| 23 | 1104 | No |
| 4 | 1159 | No |
| 8 | 1307 | Yes |
| 15 | 1513 | No |
| 13 | 1651 | No |
| 5 | 1791 | No |
| 16 | 1834 | Yes |
| 7 | 1838 | No |
| 19 | 1883 | No |
| 17 | 1973 | Yes |
| 18 | 2006 | Yes |
| 2 | 2358 | No |
| 9 | 2409 | Yes |
| 6 | 2460 | Yes |
| 11 | 2650 | Yes |
| 21 | 2652 | Yes |
| 1 | 2802 | Yes |
| 20 | 2844 | No |
| 22 | 3021 | Yes |
| 10 | 3842 | Yes |
| 14 | 5485 | No |

LGALS3 RAW DATA SORTED BY LGALS3 VALUES

FIG. 12

| PATIENT ID | LGALS3 RANK NORMALIZED VALUES | KNOWN PSA RECURRENCE ? |
|---|---|---|
| 12 | 0/22 | Yes |
| 3 | 1/22 | No |
| 23 | 2/22 | No |
| 4 | 3/22 | No |
| 8 | 4/22 | Yes |
| 15 | 5/22 | No |
| 13 | 6/22 | No |
| 5 | 7/22 | No |
| 16 | 8/22 | Yes |
| 7 | 9/22 | No |
| 19 | 10/22 | No |
| 17 | 11/22 | Yes |
| 18 | 12/22 | Yes |
| 2 | 13/22 | No |
| 9 | 14/22 | Yes |
| 6 | 15/22 | Yes |
| 11 | 16/22 | Yes |
| 21 | 17/22 | Yes |
| 1 | 18/22 | Yes |
| 20 | 19/22 | No |
| 22 | 20/22 | Yes |
| 10 | 21/22 | Yes |
| 14 | 22/22 | No |

CUT-POINT (RANK VALUE OF $0.4\overline{99}$)

RANK NORMALIZED VALUES

KAPLAN-MEIER PLOT FOR LGALS3 UNIVARIATE FEATURE

| PATIENT ID | MAGEC2 RAW MEASUREMENTS | KNOWN PSA RECURRENCE ? |
|---|---|---|
| 1 | 15 | Yes |
| 2 | 6 | No |
| 3 | 14 | No |
| 4 | 10 | No |
| 5 | 14 | No |
| 6 | 18 | Yes |
| 7 | 8 | No |
| 8 | 7 | Yes |
| 9 | 18 | Yes |
| 10 | 19 | Yes |
| 11 | 13 | Yes |
| 12 | 9 | Yes |
| 13 | 15 | No |
| 14 | 11 | No |
| 15 | 8 | No |
| 16 | 13 | Yes |
| 17 | 12 | Yes |
| 18 | 16 | Yes |
| 19 | 11 | No |
| 20 | 9 | No |
| 21 | 19 | Yes |
| 22 | 11 | Yes |
| 23 | 13 | No |

MAGEC2 RAW DATA SORTED BY PATIENT ID

FIG. 15

| PATIENT ID | MAGEC2 RAW MEASUREMENTS | KNOWN PSA RECURRENCE ? |
|---|---|---|
| 2 | 6 | No |
| 8 | 7 | Yes |
| 7 | 8 | No |
| 15 | 8 | No |
| 12 | 9 | Yes |
| 20 | 9 | No |
| 4 | 10 | No |
| 14 | 11 | No |
| 19 | 11 | No |
| 22 | 11 | Yes |
| 17 | 12 | Yes |
| 11 | 13 | Yes |
| 16 | 13 | Yes |
| 23 | 13 | No |
| 3 | 14 | No |
| 5 | 14 | No |
| 1 | 15 | Yes |
| 13 | 15 | No |
| 18 | 16 | Yes |
| 6 | 18 | Yes |
| 9 | 18 | Yes |
| 10 | 19 | Yes |
| 21 | 19 | Yes |

MAGEC2 RAW DATA SORTED BY MAGEC2 VALUES

FIG. 16

| PATIENT ID | MAGEC2 RANK NORMALIZED VALUES | KNOWN PSA RECURRENCE? |
|---|---|---|
| 2 | 0/12 | No |
| 8 | 1/12 | Yes |
| 7 | 2/12 | No |
| 15 | 2/12 | No |
| 12 | 3/12 | Yes |
| 20 | 3/12 | No |
| 4 | 4/12 | No |
| 14 | 5/12 | No |
| 19 | 5/12 | No |
| 22 | 5/12 | Yes |
| 17 | 6/12 | Yes |
| 11 | 7/12 | Yes |
| 16 | 7/12 | Yes |
| 23 | 7/12 | No |
| 3 | 8/12 | No |
| 5 | 8/12 | No |
| 1 | 9/12 | Yes |
| 13 | 9/12 | No |
| 18 | 10/12 | Yes |
| 6 | 11/12 | Yes |
| 9 | 11/12 | Yes |
| 10 | 12/12 | Yes |
| 21 | 12/12 | Yes |

CUT-POINT (RANK VALUE OF $0.4\overline{99}$)

NORMALIZED RANK VALUES

P-VALUE = 0.05880

KAPLAN-MEIER PLOT FOR MAGEC2 UNIVARIATE FEATURE

IHC_DIST_CD163(+)_CD3(+)CD8(-)
RAW MEASUREMENTS

| PATIENT ID | | KNOWN PSA RECURRENCE ? |
|---|---|---|
| 1 | 582 | Yes |
| 2 | 621 | No |
| 3 | 1417 | No |
| 4 | 1120 | No |
| 5 | 1679 | No |
| 6 | 1601 | Yes |
| 7 | 634 | No |
| 8 | 511 | Yes |
| 9 | 687 | Yes |
| 10 | 728 | Yes |
| 11 | 1803 | Yes |
| 12 | 1220 | Yes |
| 13 | 2062 | No |
| 14 | 991 | No |
| 15 | 738 | No |
| 16 | 705 | Yes |
| 17 | 659 | Yes |
| 18 | 899 | Yes |
| 19 | 745 | No |
| 20 | 1198 | No |
| 21 | 681 | Yes |
| 22 | 728 | Yes |
| 23 | 1427 | No |

IHC_DIST_CD163(+)_CD3(+)CD8(-)
RAW DATA SORTED BY PATIENT ID

FIG. 19

IHC_DIST_CD163(+)_CD3(+)CD8(-)
RAW MEASUREMENTS

| PATIENT ID | | KNOWN PSA RECURRENCE ? |
|---|---|---|
| 8 | 511 | Yes |
| 1 | 582 | Yes |
| 2 | 621 | No |
| 7 | 634 | No |
| 17 | 659 | Yes |
| 21 | 681 | Yes |
| 9 | 687 | Yes |
| 16 | 705 | Yes |
| 22 | 728 | Yes |
| 10 | 728 | Yes |
| 15 | 738 | No |
| 19 | 745 | No |
| 18 | 899 | Yes |
| 14 | 991 | No |
| 4 | 1120 | No |
| 20 | 1198 | No |
| 12 | 1220 | Yes |
| 3 | 1417 | No |
| 23 | 1427 | No |
| 6 | 1601 | Yes |
| 5 | 1679 | No |
| 11 | 1803 | Yes |
| 13 | 2062 | No |

IHC_DIST_CD163(+)_CD3(+)CD8(-) RAW
DATA SORTED BY
IHC_DIST_CD163(+)_CD(+)CD8(-) VALUE

FIG. 20

| PATIENT ID | IHC_DIST_CD163(+)_CD3(+)CD8(-) RANK NORMALIZED VALUES | KNOWN PSA RECURRENCE? |
|---|---|---|
| 8 | 0/22 | Yes |
| 1 | 1/22 | Yes |
| 2 | 2/22 | No |
| 7 | 3/22 | No |
| 17 | 4/22 | Yes |
| 21 | 5/22 | Yes |
| 9 | 6/22 | Yes |
| 16 | 7/22 | Yes |
| 22 | 8/22 | Yes |
| 10 | 9/22 | Yes |
| 15 | 10/22 | No |
| 19 | 11/22 | No |
| 18 | 12/22 | Yes |
| 14 | 13/22 | No |
| 4 | 14/22 | No |
| 20 | 15/22 | No |
| 12 | 16/22 | Yes |
| 3 | 17/22 | No |
| 23 | 18/22 | No |
| 6 | 19/22 | Yes |
| 5 | 20/22 | No |
| 11 | 21/22 | Yes |
| 13 | 22/22 | No |

CUT-POINT (RANK VALUE OF $0.4\overline{99}$)

RANK NORMALIZED VALUES

KAPLAN-MEIER PLOT FOR IHC_DIST_CD163(+)_CD3(+)CD8(-) UNIVARIATE FEATURE

| | SYMBOL | NOTATION |
|---|---|---|
| SCORE SM1 FOR PATIENT K = (f1 FOR PATIENT K) x (f2 FOR PATIENT K) | ⟷ | . and . |
| SCORE SM2 FOR PATIENT K = ((1-f1) FOR PATIENT K) x (f2 FOR PATIENT K) | ⟶ | not . and . |
| SCORE SM3 FOR PATIENT K = (f1 FOR PATIENT K) x ((1-f2) FOR PATIENT K) | ⟵ | . and . not |
| SCORE SM4 FOR PATIENT K = ((1-f1) FOR PATIENT K) x ((1-f2) FOR PATIENT K) | — | not . and . not |

BIVARIATE SCORING METHODS
AND NOTATIONS

FIG. 23

| PATIENT ID | LGALS3 RANK VALUES (f1) | PATIENT ID | MAGEC2 RANK VALUES (f2) | PATIENT ID | f1 x f2 SM1 | PATIENT ID | f1 x f2 SORTED |
|---|---|---|---|---|---|---|---|
| 1 | 18/22 | 1 | 9/12 | 1 | 0.6136 | 2 | 0.0000 |
| 2 | 13/22 | 2 | 0/12 | 2 | 0.0000 | 12 | 0.0000 |
| 3 | 1/22 | 3 | 8/12 | 3 | 0.0303 | 8 | 0.0152 |
| 4 | 3/22 | 4 | 4/12 | 4 | 0.0455 | 3 | 0.0303 |
| 5 | 7/22 | 5 | 8/12 | 5 | 0.2121 | 15 | 0.0379 |
| 6 | 15/22 | 6 | 11/12 | 6 | 0.6250 | 4 | 0.0455 |
| 7 | 9/22 | 7 | 2/12 | 7 | 0.0682 | 23 | 0.0530 |
| 8 | 4/22 | 8 | 1/12 | 8 | 0.0152 | 7 | 0.0682 |
| 9 | 14/22 | 9 | 11/12 | 9 | 0.5833 | 19 | 0.1894 |
| 10 | 21/22 | 10 | 12/12 | 10 | 0.9545 | 13 | 0.2045 |
| 11 | 16/22 | 11 | 7/12 | 11 | 0.4242 | 5 | 0.2121 |
| 12 | 0/22 | 12 | 3/12 | 12 | 0.0000 | 16 | 0.2121 |
| 13 | 6/22 | 13 | 9/12 | 13 | 0.2045 | 20 | 0.2159 |
| 14 | 22/22 | 14 | 5/12 | 14 | 0.4167 | 17 | 0.2500 |
| 15 | 5/22 | 15 | 2/12 | 15 | 0.0379 | 22 | 0.3788 |
| 16 | 8/22 | 16 | 7/12 | 16 | 0.2121 | 14 | 0.4167 |
| 17 | 11/22 | 17 | 6/12 | 17 | 0.2500 | 11 | 0.4242 |
| 18 | 12/22 | 18 | 10/12 | 18 | 0.4545 | 18 | 0.4545 |
| 19 | 10/22 | 19 | 5/12 | 19 | 0.1894 | 9 | 0.5833 |
| 20 | 19/22 | 20 | 3/12 | 20 | 0.2159 | 1 | 0.6136 |
| 21 | 17/22 | 21 | 12/12 | 21 | 0.7727 | 6 | 0.6250 |
| 22 | 20/22 | 22 | 5/12 | 22 | 0.3788 | 21 | 0.7727 |
| 23 | 2/22 | 23 | 7/12 | 23 | 0.0530 | 10 | 0.9545 |

CUT-POINT = 0.2121 (THE MEDIAN VALUE)

CALCULATION OF LGALS3-TO-MAGEC2 VALUES FOR SM1

CALCULATION OF LGALS3-TO-MAGEC2 VALUES FOR SM2

| PATIENT ID | (1-f1) × f2<br>SM2 | PATIENT ID | (1-f1) × f2<br>SORTED |
|---|---|---|---|
| 1 | 0.1364 | 2 | 0.0000 |
| 2 | 0.0000 | 14 | 0.0000 |
| 3 | 0.6364 | 20 | 0.0341 |
| 4 | 0.2879 | 22 | 0.0379 |
| 5 | 0.4545 | 10 | 0.0455 |
| 6 | 0.2917 | 8 | 0.0682 |
| 7 | 0.0985 | 7 | 0.0985 |
| 8 | 0.0682 | 15 | 0.1288 |
| 9 | 0.3333 | 1 | 0.1364 |
| 10 | 0.0455 | 11 | 0.1591 |
| 11 | 0.1591 | 19 | 0.2273 |
| 12 | 0.2500 | 21 | 0.2273 |
| 13 | 0.5455 | 12 | 0.2500 |
| 14 | 0.0000 | 17 | 0.2500 |
| 15 | 0.1288 | 4 | 0.2879 |
| 16 | 0.3712 | 6 | 0.2917 |
| 17 | 0.2500 | 9 | 0.3333 |
| 18 | 0.3788 | 16 | 0.3712 |
| 19 | 0.2273 | 18 | 0.3788 |
| 20 | 0.0341 | 5 | 0.4545 |
| 21 | 0.2273 | 23 | 0.5303 |
| 22 | 0.0379 | 13 | 0.5455 |
| 23 | 0.5303 | 3 | 0.6364 |

CUT-POINT = 0.2273 (THE MEDIAN VALUE)

FIG. 26

CALCULATION OF LGALS3-TO-MAGEC2 VALUES FOR SM3

| PATIENT ID | f1 × (1-f2)<br>SM3 | PATIENT ID | f1 × (1-f2)<br>SORTED |
|---|---|---|---|
| 1 | 0.2045 | 10 | 0.0000 |
| 2 | 0.5909 | 12 | 0.0000 |
| 3 | 0.0152 | 21 | 0.0000 |
| 4 | 0.0909 | 3 | 0.0152 |
| 5 | 0.1061 | 23 | 0.0379 |
| 6 | 0.0568 | 9 | 0.0530 |
| 7 | 0.3409 | 6 | 0.0568 |
| 8 | 0.1667 | 13 | 0.0682 |
| 9 | 0.0530 | 4 | 0.0909 |
| 10 | 0.0000 | 18 | 0.0909 |
| 11 | 0.3030 | 5 | 0.1061 |
| 12 | 0.0000 | 16 | 0.1515 |
| 13 | 0.0682 | 8 | 0.1667 |
| 14 | 0.5833 | 15 | 0.1894 |
| 15 | 0.1894 | 1 | 0.2045 |
| 16 | 0.1515 | 17 | 0.2500 |
| 17 | 0.2500 | 19 | 0.2652 |
| 18 | 0.0909 | 11 | 0.3030 |
| 19 | 0.2652 | 7 | 0.3409 |
| 20 | 0.6477 | 22 | 0.5303 |
| 21 | 0.0000 | 14 | 0.5833 |
| 22 | 0.5303 | 2 | 0.5909 |
| 23 | 0.0379 | 20 | 0.6477 |

CUT-POINT = 0.1515 (THE MEDIAN VALUE)

| PATIENT ID | SM4 $(1-f1) \times (1-f2)$ | PATIENT ID | $(1-f1) \times (1-f2)$ SORTED |
|---|---|---|---|
| 1  | 0.0455 | 10 | 0.0000 |
| 2  | 0.4091 | 14 | 0.0000 |
| 3  | 0.3182 | 21 | 0.0000 |
| 4  | 0.5758 | 6  | 0.0265 |
| 5  | 0.2273 | 9  | 0.0303 |
| 6  | 0.0265 | 1  | 0.0455 |
| 7  | 0.4924 | 22 | 0.0530 |
| 8  | 0.7500 | 18 | 0.0758 |
| 9  | 0.0303 | 20 | 0.1023 |
| 10 | 0.0000 | 11 | 0.1136 |
| 11 | 0.1136 | 13 | 0.1818 |
| 12 | 0.7500 | 5  | 0.2273 |
| 13 | 0.1818 | 17 | 0.2500 |
| 14 | 0.0000 | 16 | 0.2652 |
| 15 | 0.6439 | 3  | 0.3182 |
| 16 | 0.2652 | 19 | 0.3182 |
| 17 | 0.2500 | 23 | 0.3788 |
| 18 | 0.0758 | 2  | 0.4091 |
| 19 | 0.3182 | 7  | 0.4924 |
| 20 | 0.1023 | 4  | 0.5758 |
| 21 | 0.0000 | 8  | 0.7500 |
| 22 | 0.0530 | 12 | 0.7500 |
| 23 | 0.3788 | 15 | 0.6439 |

CUT-POINT = 0.2272 (THE MEDIAN VALUE)

CALCULATION OF LGALS3-TO-MAGEC2 VALUES FOR SM4

FIG. 27

| LGALS3-TO-MAGEC2 SCORING METHOD (SM) | DETERMINED P-VALUE |
|---|---|
| SM1 | 0.0009008 |
| SM2 | 0.9806 |
| SM3 | 0.8034 |
| SM4 | 0.006845 |

SCORING METHOD = SM1
(THE SMALLEST P-VALUE DETERMINES THE SCORING METHOD USED)

DETERMINE SCORING METHOD

KAPLAN-MEIER PLOT FOR THE LGALS3-TO-MAGEC2 BIVARIATE FEATURE (SM=SM1)

| PATIENT ID | IHC_DIST_CD163(+)_CD3(+)CD8(-) RANK VALUES (f1) | PATIENT ID | MAGEC2 RANK VALUES (f2) | PATIENT ID | f1 x f2 SM1 | PATIENT ID | f1 x f2 SORTED |
|---|---|---|---|---|---|---|---|
| 1 | 1/22 | 1 | 9/12 | 1 | 0.0341 | 2 | 0.0000 |
| 2 | 2/22 | 2 | 0/12 | 2 | 0.0000 | 8 | 0.0000 |
| 3 | 17/22 | 3 | 8/12 | 3 | 0.5152 | 7 | 0.0227 |
| 4 | 14/22 | 4 | 4/12 | 4 | 0.2121 | 1 | 0.0341 |
| 5 | 20/22 | 5 | 8/12 | 5 | 0.6061 | 15 | 0.0758 |
| 6 | 19/22 | 6 | 11/12 | 6 | 0.7917 | 17 | 0.0909 |
| 7 | 3/22 | 7 | 2/12 | 7 | 0.0227 | 22 | 0.1515 |
| 8 | 0/22 | 8 | 1/12 | 8 | 0.0000 | 20 | 0.1705 |
| 9 | 6/22 | 9 | 11/12 | 9 | 0.2500 | 12 | 0.1818 |
| 10 | 9/22 | 10 | 12/12 | 10 | 0.4091 | 16 | 0.1856 |
| 11 | 21/22 | 11 | 7/12 | 11 | 0.5568 | 19 | 0.2083 |
| 12 | 16/22 | 12 | 3/12 | 12 | 0.1818 | 4 | 0.2121 |
| 13 | 22/22 | 13 | 9/12 | 13 | 0.7500 | 21 | 0.2273 |
| 14 | 13/22 | 14 | 5/12 | 14 | 0.2462 | 14 | 0.2462 |
| 15 | 10/22 | 15 | 2/12 | 15 | 0.0758 | 9 | 0.2500 |
| 16 | 7/22 | 16 | 7/12 | 16 | 0.1856 | 10 | 0.4091 |
| 17 | 4/22 | 17 | 6/12 | 17 | 0.0909 | 18 | 0.4545 |
| 18 | 12/22 | 18 | 10/12 | 18 | 0.4545 | 23 | 0.4773 |
| 19 | 11/22 | 19 | 5/12 | 19 | 0.2083 | 3 | 0.5152 |
| 20 | 15/22 | 20 | 3/12 | 20 | 0.1705 | 11 | 0.5568 |
| 21 | 5/22 | 21 | 12/12 | 21 | 0.2273 | 5 | 0.6061 |
| 22 | 8/22 | 22 | 5/12 | 22 | 0.1515 | 13 | 0.7500 |
| 23 | 18/22 | 23 | 7/12 | 23 | 0.4773 | 6 | 0.7917 |

CUT-POINT = 0.2121 (THE MEDIAN VALUE)

CALCULATION OF IHC_DIST_CD163(+)_CD3(+)CD8(-)-TO-MAGEC2 VALUES FOR SM1

FIG. 30

| PATIENT ID | SM2 $(1-f1) \times f2$ | PATIENT ID | $(1-f1) \times f2$ SORTED |
|---|---|---|---|
| 1 | 0.7159 | 2 | 0.0000 |
| 2 | 0.0000 | 13 | 0.0000 |
| 3 | 0.1515 | 11 | 0.0265 |
| 4 | 0.1212 | 5 | 0.0606 |
| 5 | 0.0606 | 12 | 0.0682 |
| 6 | 0.1250 | 20 | 0.0795 |
| 7 | 0.1439 | 8 | 0.0833 |
| 8 | 0.0833 | 15 | 0.0909 |
| 9 | 0.6667 | 23 | 0.1061 |
| 10 | 0.5909 | 4 | 0.1212 |
| 11 | 0.0265 | 6 | 0.1250 |
| 12 | 0.0682 | 7 | 0.1439 ← CUT-POINT = 0.1439 (THE MEDIAN VALUE) |
| 13 | 0.0000 | 3 | 0.1515 |
| 14 | 0.1750 | 14 | 0.1750 |
| 15 | 0.0909 | 19 | 0.2083 |
| 16 | 0.3977 | 22 | 0.2652 |
| 17 | 0.4091 | 18 | 0.3788 |
| 18 | 0.3788 | 16 | 0.3977 |
| 19 | 0.2083 | 17 | 0.4091 |
| 20 | 0.0795 | 10 | 0.5909 |
| 21 | 0.7727 | 9 | 0.6667 |
| 22 | 0.2652 | 1 | 0.7159 |
| 23 | 0.1061 | 21 | 0.7727 |

CALCULATION OF IHC_CD163(+)_CD3(+)CD8(-)-TO-MAGEC2 VALUES FOR SM2

FIG. 31

| PATIENT ID | SM3 $f1 \times (1-f2)$ | PATIENT ID | $f1 \times (1-f2)$ SORTED |
|---|---|---|---|
| 1 | 0.0114 | 10 | 0.0000 |
| 2 | 0.0909 | 8 | 0.0000 |
| 3 | 0.2576 | 21 | 0.0000 |
| 4 | 0.4242 | 1 | 0.0114 |
| 5 | 0.3030 | 9 | 0.0227 |
| 6 | 0.0720 | 6 | 0.0720 |
| 7 | 0.1136 | 2 | 0.0909 |
| 8 | 0.0000 | 17 | 0.0909 |
| 9 | 0.0227 | 18 | 0.0909 |
| 10 | 0.0000 | 7 | 0.1136 |
| 11 | 0.3977 | 16 | 0.1326 |
| 12 | 0.5455 | 22 | 0.2121 ← CUT-POINT = 0.2121 (THE MEDIAN VALUE) |
| 13 | 0.2500 | 13 | 0.2500 |
| 14 | 0.3447 | 3 | 0.2576 |
| 15 | 0.3788 | 19 | 0.2917 |
| 16 | 0.1326 | 5 | 0.3030 |
| 17 | 0.0909 | 23 | 0.3409 |
| 18 | 0.0909 | 14 | 0.3447 |
| 19 | 0.2917 | 15 | 0.3788 |
| 20 | 0.5114 | 11 | 0.3977 |
| 21 | 0.0000 | 4 | 0.4242 |
| 22 | 0.2121 | 20 | 0.5114 |
| 23 | 0.3409 | 12 | 0.5455 |

CALCULATION OF IHC_CD163(+)_CD3(+)CD8(-)-TO-MAGEC2 VALUES FOR SM3

FIG. 32

| PATIENT ID | SM4 $(1-f1) \times (1-f2)$ | PATIENT ID | $(1-f1) \times (1-f2)$ SORTED |
|---|---|---|---|
| 1 | 0.2386 | 10 | 0.0000 |
| 2 | 0.9091 | 13 | 0.0000 |
| 3 | 0.0758 | 21 | 0.0000 |
| 4 | 0.2424 | 6 | 0.0114 |
| 5 | 0.0303 | 11 | 0.0189 |
| 6 | 0.0114 | 5 | 0.0303 |
| 7 | 0.7197 | 9 | 0.0606 |
| 8 | 0.9167 | 3 | 0.0758 |
| 9 | 0.0606 | 18 | 0.0758 |
| 10 | 0.0000 | 23 | 0.0758 |
| 11 | 0.0189 | 12 | 0.2045 |
| 12 | 0.2045 | 1 | 0.2386 |
| 13 | 0.0000 | 14 | 0.2386 |
| 14 | 0.2386 | 20 | 0.2386 |
| 15 | 0.4545 | 4 | 0.2424 |
| 16 | 0.2841 | 16 | 0.2841 |
| 17 | 0.4091 | 19 | 0.2917 |
| 18 | 0.0758 | 22 | 0.3712 |
| 19 | 0.2917 | 17 | 0.4091 |
| 20 | 0.2386 | 15 | 0.4545 |
| 21 | 0.0000 | 7 | 0.7197 |
| 22 | 0.3712 | 2 | 0.9091 |
| 23 | 0.0758 | 8 | 0.9167 |

CUT-POINT = 0.2386 (THE MEDIAN VALUE)

CALCULATION OF IHC_CD163(+)_CD3(+)CD8(-)-TO-MAGEC2 VALUES FOR SM4

FIG. 33

| IHC_CD163(+)_CD3(+)CD8(-)-TO-MAGEC2 SCORING METHOD (SM) | DETERMINED P-VALUE |
|---|---|
| SM1 | 0.9605 |
| SM2 | 0.04208 |
| SM3 | 0.001686 |
| SM4 | 0.5164 |

SCORING METHOD = SM3 (THE SMALLEST P-VALUE DETERMINES THE SCORING METHOD USED)

DETERMINE SCORING METHOD

P-VALUE = 0.001686

KAPLAN-MEIER PLOT FOR THE IHC_DIST_CD163(+)_CD3(+)CD8(-)-TO-MAGEC2 BIVARIATE FEATURE (SM=SM3)

| UNIVARIATE FEATURE | RAW MEASUREMENTS OF NEW PATIENT TO BE SCORED |
|---|---|
| LGALS3 | 2403 |
| MAGEC2 | 5 |
| IHC_DIST_CD163(+)_CD3(+)CD8(-) | 700 |

DIAGNOSTIC PHASE
RAW MEASUREMENTS OF A PATIENT

DIAGNOSTIC PHASE
DETERMINE A LGALS3 UNIVARIATE FEATURE
SCORE VALUE FOR THE NEW PATIENT

| MAGEC2 RAW MEASUREMENT | PATIENT ID | RANK VALUE |
|---|---|---|
| 6 | 2 | 0/12 |
| 7 | 8 | 1/12 |
| 8 | 7 | 2/12 |
| 8 | 15 | 2/12 |
| 9 | 12 | 3/12 |
| 9 | 20 | 3/12 |
| 10 | 4 | 4/12 |
| 11 | 14 | 5/12 |
| 11 | 19 | 5/12 |
| 11 | 22 | 5/12 |
| 12 | 17 | 6/12 |
| 13 | 11 | 7/12 |
| 13 | 16 | 7/12 |
| 13 | 23 | 7/12 |
| 14 | 3 | 8/12 |
| 14 | 5 | 8/12 |
| 15 | 1 | 9/12 |
| 15 | 13 | 9/12 |
| 16 | 18 | 10/12 |
| 18 | 6 | 11/12 |
| 18 | 9 | 11/12 |
| 19 | 10 | 12/12 |
| 19 | 21 | 12/12 |

THE NEW PATIENT'S MAGEC2 RAW MEASUREMENT IS 5

NEW PATIENT'S RANK VALUE = $\frac{10.5}{12}$

LONGER SURVIVAL (SEE FIG. 18)

CUT-POINT (RANK VALUE OF $0.4\overline{99}$)

SHORTER SURVIVAL (SEE FIG. 18)

NEW PATIENT'S RANK VALUE IS LOWER THAN CUT-POINT AND THEREFORE WITHIN THE LONGER SURVIVAL GROUP, THEREFORE $S_{MAGEC2} = 0$

DIAGNOSTIC PHASE

DETERMINE A MAGEC2 UNIVARIATE FEATURE SCORE VALUE FOR THE NEW PATIENT

FIG. 38

IHC_DIST_CD163(+)_CD3(+)CD8(-)
RAW MEASUREMENT

| PATIENT ID | RANK VALUE |
|---|---|
| 511 | 8 | 0/22 |
| 582 | 1 | 1/22 |
| 621 | 2 | 2/22 |
| 634 | 7 | 3/22 |
| 659 | 17 | 4/22 |
| 681 | 21 | 5/22 |
| 687 | 9 | 6/22 |
| 705 | 16 | 7/22 |
| 728 | 22 | 8/22 |
| 728 | 10 | 9/22 |
| 738 | 15 | 10/22 |
| 745 | 19 | 11/22 |
| 899 | 18 | 12/22 |
| 991 | 14 | 13/22 |
| 1120 | 4 | 14/22 |
| 1198 | 20 | 15/22 |
| 1220 | 12 | 16/22 |
| 1417 | 3 | 17/22 |
| 1427 | 23 | 18/22 |
| 1601 | 6 | 19/22 |
| 1679 | 5 | 20/22 |
| 1803 | 11 | 21/22 |
| 2062 | 13 | 22/22 |

THE NEW PATIENT'S IHC_DIST_CD163(+)_CD3(+)CD8(-) RAW MEASUREMENT IS 700

SHORTER SURVIVAL (SEE FIG. 20)

NEW PATIENT'S RANK VALUE = $\frac{6.5}{22}$

CUT-POINT (RANK VALUE OF $0.4\overline{99}$)

LONGER SURVIVAL (SEE FIG. 20)

NEW PATIENT'S RANK VALUE IS LOWER THAN CUT-POINT AND THEREFORE WITHIN THE SHORTER SURVIVAL GROUP, THEREFORE $S_{IHC} = 1$

DIAGNOSTIC PHASE

DETERMINE A IHC_DIST_CD163(+)_CD3(+)CD8(-) UNIVARIATE FEATURE SCORE VALUE FOR THE NEW PATIENT

FIG. 39

PSA Recurrence Score = 0, if $(S_{LGALS3}+S_{MAGEC2}+S_{IHC}+S_{(LGALS3 - MAGEC2)}+S_{(IHC - MAGEC2)}) < 2.5$ $= 1$, if $(S_{LGALS3}+S_{MAGEC2}+S_{IHC}+S_{(LGALS3 - MAGEC2)}+S_{(IHC - MAGEC2)}) > 2.5$

FUNCTION THAT DETERMINES THE PSA RECURRENCE SCORE FOR THE NEW PATIENT

FIG. 42

A HIGH SCORE INDICATES A HIGH PROBABILITY OF RECURRENCE $(S_{LGALS3}+S_{MAGEC2}+S_{IHC}+S_{(LGALS3 - MAGEC2)}+S_{(IHC - MAGEC2)}) = (1+0+1+0+0) = 2$ because 2 < 2.5 the "PSA Recurrence Score" is 0.

DIAGNOSTIC PHASE

DETERMINE THE PSA RECURRENCE SCORE FOR THE NEW PATIENT

FIG. 43

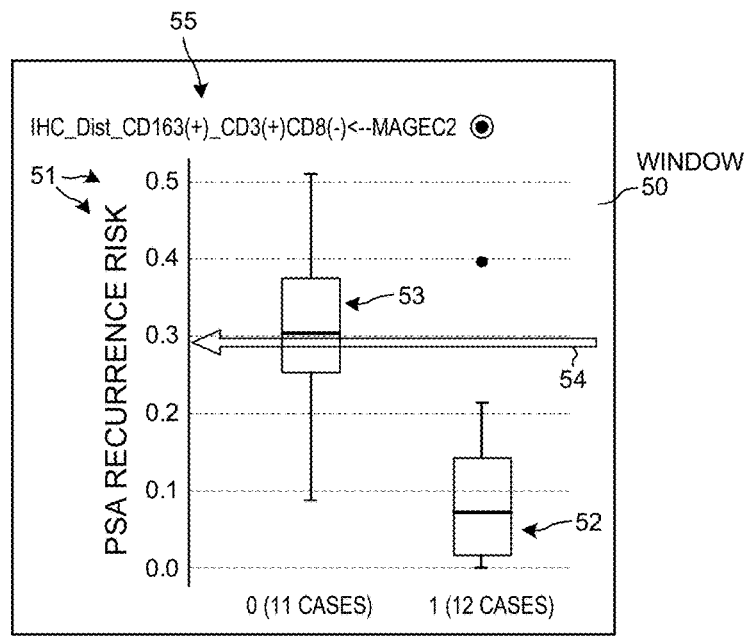

FIG. 44

PREDICTING PROSTATE CANCER RECURRENCE USING A PROGNOSTIC MODEL THAT COMBINES IMMUNOHISTOCHEMICAL STAINING AND GENE EXPRESSION PROFILING

CROSS REFERENCE TO RELATED APPLICATION

This application claims the benefit under 35 U.S.C. § 119 of provisional application Ser. No. 62/629,591, entitled "Predicting Prostate Cancer Recurrence Using A Prognostic Model That Combines Immunohistochemical Staining And Gene Expression Profiling", filed on Feb. 12, 2018, by Guenter Schmidt. The subject matter of provisional application Ser. No. 62/629,591 is incorporated herein by reference.

TECHNICAL FIELD

The present invention relates to systems and methods for detecting cancer and predicting the recurrence of cancer, and more particularly relates to systems and methods for predicting the recurrence of prostate cancer PSA recurrence.

BACKGROUND INFORMATION

A cancer patient can be treated such that the cancer goes into remission. Knowing whether and when the cancer might later come out of remission and recur would, for many reasons, be beneficial. Having such information may facilitate making better clinical and treatment decisions. Having such information may also allow the patient to improve the patient's quality of life, and to make better life decisions. An improved system and method for determining the likelihood of cancer recurrence is desired.

SUMMARY

A method for providing a graphical indication of whether a patient will have a recurrence of a cancer uses univariate and bivariate prognostic features that were generated as part of a minimal spanning tree (MST). The method involves determining a first value of a first feature and a second value of a second feature. The first value is measured based on an object detected in a digital image of a first tissue slice that has been stained with a protein-specific immunohistochemical (IHC) biomarker. The first tissue slice was cut from a formalin fixed paraffin embedded (FFPE) tissue sample of cancer tissue from the patient. The second value is measured based on objects marked with an mRNA-specific probe biomarker detected in a second tissue slice that was cut from the FFPE tissue sample. The first feature is the univariate prognostic feature for the recurrence of the cancer in a cohort of patients exhibiting the cancer. A combination of the first feature and the second feature is the bivariate prognostic feature for the recurrence of the cancer in the cohort of patients. The first feature and the second feature are elements of the minimal spanning tree that is constructed from univariate and bivariate prognostic features for the recurrence of the cancer in the cohort. Nodes of the minimal spanning tree represent the univariate prognostic features, edges of the minimal spanning tree represent the bivariate prognostic features, and weights of the edges represent prognostic significance of the bivariate prognostic features. The graphical indication of the combination of the first value and the second value is displayed on a graphical user interface to illustrate whether the patient will have a recurrence of the cancer.

A method for generating a network of prognostic features for cancer recurrence of a cohort of cancer patients involves computing bivariate prognostic features that are the edges of the network. A set of immunohistochemical-based (IHC-based) values of IHC-based features is measured based on a tissue sample of a tumor of each cancer patient in the cohort. A set of gene expression values of gene expression features is measured based on the tissue sample of the tumor of each cancer patient in the cohort. A set of bivariate prognostic features is computed that exhibit significant prognostic value on the cancer recurrence. All or a portion of the network is displayed on a computer display. A first node of the network represents one of the set of IHC-based features. A second node of the network represents one of the set of gene expression features. An edge of the network that extends between the first node and the second node represents one of the set of bivariate prognostic features.

An analysis and display system generates and displays a score indicative of whether cancer will recur in a patient. In a learning phase, tumor tissue from each one of many patients is obtained and analyzed. For each of these patients, it is known whether the patient suffered a recurrence of cancer, and this cancer recurrence information is loaded into the system. A univariate phenomic feature of the tumor tissue is measured and a corresponding univariate phenomic feature is defined. The univariate phenomic feature may be measured through image analysis of digital images taken of tissue slices stained with IHC-based stains. A univariate genomic feature of the tissue is also measured. This may entail obtaining a probe count indicative of a degree of expression of a particular gene. A bivariate feature is then defined using both the phenomic and genomic information. In this way, many univariate features can be measured. A bivariate feature can be defined for the relationship between any two of the univariate features. A bivariate feature for the relationship between each pair of univariate features is defined. Once all this information has been collected and all the features have been calculated and defined, the system employs a thinning method to eliminate those features that do not have a substantial prognostic value in predicting the recurrence of cancer in a patient. The result of this elimination of unimportant features is a Minimal Spanning Tree (MST). The MST is a network (also called a graph). It includes the features of substantial prognostic importance.

In one novel aspect, some of the nodes (bubbles) of the MST network represent phenomic features, and others of the nodes represent genomic features. The edges (arrows) between nodes represent bivariate features. Some of the edges represent bivariate features that are based on both phenomic feature information and genomic feature information. The method of using phenomic feature information along with genomic feature information in the prediction of cancer recurrence allows additional feature measurements to be brought to bear in the determination of the score, as compared to methods that only use genomic information.

In another novel aspect, a user of the system can cause a rendering of the MST network to be displayed on the display of the system. The nodes of univariate features that have more prognostic importance are rendered to be larger, whereas the nodes of univariate features that have less prognostic importance are rendered to be smaller. Edges in the network that have more prognostic importance are rendered as thicker lines, whereas edges in the network that have less prognostic importance are rendered as thinner lines. The type of bivariate relationship (one of four "fuzzy logic" combinations) that was determined in the learning phase to have the most prognostic importance is indicated in the MST network by the type of arrow or line that is representing the edge.

In a diagnostic phase, a score is to be generated for a new patient. A diagnostic test that involves collecting information on only a relatively small number of the features is developed using the network as displayed on the system. In one example, raw measurement information on only three univariate features need be collected from the patient. One of the univariate features is a phenomic feature, and the other two univariate features are genomic features. A tissue sample is taken from the patient and both the raw phenomic data as well as the raw genomic data is obtained from the sample. From the raw measurement data, a score value for each univariate feature (each univariate feature used in the diagnostic test) is calculated. In the example in which there are three univariate features involved in the diagnostic test, raw measurement data for each of these three univariate features is obtained. From this raw data, a score value for each of the three univariate features is calculated. In addition, the raw data is used to calculate a score value for each of the two bivariate features (edges in the network) between these three univariate features. The overall score is a function of the underlying feature score values. In one example, each of the underlying score values is either a "1" (representing a "yes" vote), or a "0" (representing a "no" vote). There is one score value for each of the three univariate phenomic features, and there is one score value for each of the two bivariate features, for a total of five score values. The function is a majority voting function. The overall score is therefore a majority vote of the five votes provided by the five underlying features. The resulting overall score, which is indicative of whether cancer will recur in the patient, is then displayed on the display of the system.

Multiple different diagnostic tests can be developed by inspecting the network after the learning phase, and by selecting features that have notably high prognostic importance. The example outlined above of a test involving three univariate features and two bivariate features is presented for illustrative purposes. Although an example of the system is presented where the score is to be indicative of whether the patient will suffer a recurrence of prostate cancer, the system has general applicability. For example, the system is usable to generate a score indicative of whether a patient will suffer a recurrence of another type of cancer, such as lung cancer, or breast cancer.

Further details and embodiments and methods are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 5 is a table that sets forth thirty-two univariate features that are determined to have significant prognostic value in the prediction of the recurrence of cancer (specifically prostate cancer).

FIG. 11 is a diagram that sets forth LGALS3 raw measurements used in the learning phase of the system.

FIG. 12 shows how the information in the rows of FIG. 11 is reordered (i.e., "ranked") so that the top row is for the patient having the smallest raw measurement count, and so that the bottom row is for the patient having the largest raw measurement count.

FIG. 15 is a diagram that sets forth MAGEC2 raw measurements used in the learning phase of the system.

FIG. 16 shows how the information in the rows of FIG. 15 is reordered (i.e., "ranked") so that the top row is for the patient having the smallest raw measurement count, and so that the bottom row is for the patient having the largest raw measurement count.

FIG. 19 is a diagram that sets forth IHC_DIST_CD163 (+)_CD3(+)CD8(−) raw measurements used in the learning phase of the system.

FIG. 20 shows how the information in the rows of FIG. 15 is reordered (i.e., "ranked") so that the top row is for the patient having the smallest raw measurement count, and so that the bottom row is for the patient having the largest raw measurement count.

FIG. 23 is a table that shows the four "fuzzy logic" bivariate scoring methods.

FIG. 24 is a diagram that shows how LGALS3-to-MAGEC2 values for scoring method SM1 are calculated.

FIG. 25 is a diagram that shows how LGALS3-to-MAGEC2 values for scoring method SM2 are calculated.

FIG. 26 is a diagram that shows how LGALS3-to-MAGEC2 values for scoring method SM3 are calculated.

FIG. 27 is a diagram that shows how LGALS3-to-MAGEC2 values for scoring method SM4 are calculated.

FIG. 30 is a diagram that shows how IHC_DIST_CD163 (+)_CD3(+)CD8(−)-to-MAGEC2 values for scoring method SM1 are calculated.

FIG. 31 is a diagram that shows how IHC_DIST_CD163 (+)_CD3(+)CD8(−)-to-MAGEC2 values for scoring method SM2 are calculated.

FIG. 32 is a diagram that shows how IHC_DIST_CD163 (+)_CD3(+)CD8(−)-to-MAGEC2 values for scoring method SM3 are calculated.

FIG. 33 is a diagram that shows how IHC_DIST_CD163 (+)_CD3(+)CD8(−)-to-MAGEC2 values for scoring method SM4 are calculated.

FIG. 38 shows how a score value is determined in the diagnostic phase for the MAGEC2 univariate feature.

FIG. 39 shows how a score value is determined in the diagnostic phase for the IHC_DIST_CD163(+)_CD3(+) CD8(−) univariate feature.

FIG. 42 sets forth the function that is used to determine the overall score from the underlying five feature score values.

FIG. 43 shows how the function of FIG. 42 is applied in the case of the new patient whose overall score is being determined in the diagnostic phase.

FIG. 44 is a diagram that shows the graphical user interface visualization element 51 that is displayed in the window 50 on the display 9 of the system 1 of FIG. 1.

DETAILED DESCRIPTION

Reference will now be made in detail to some embodiments of the invention, examples of which are illustrated in the accompanying drawings.

Figure 1:
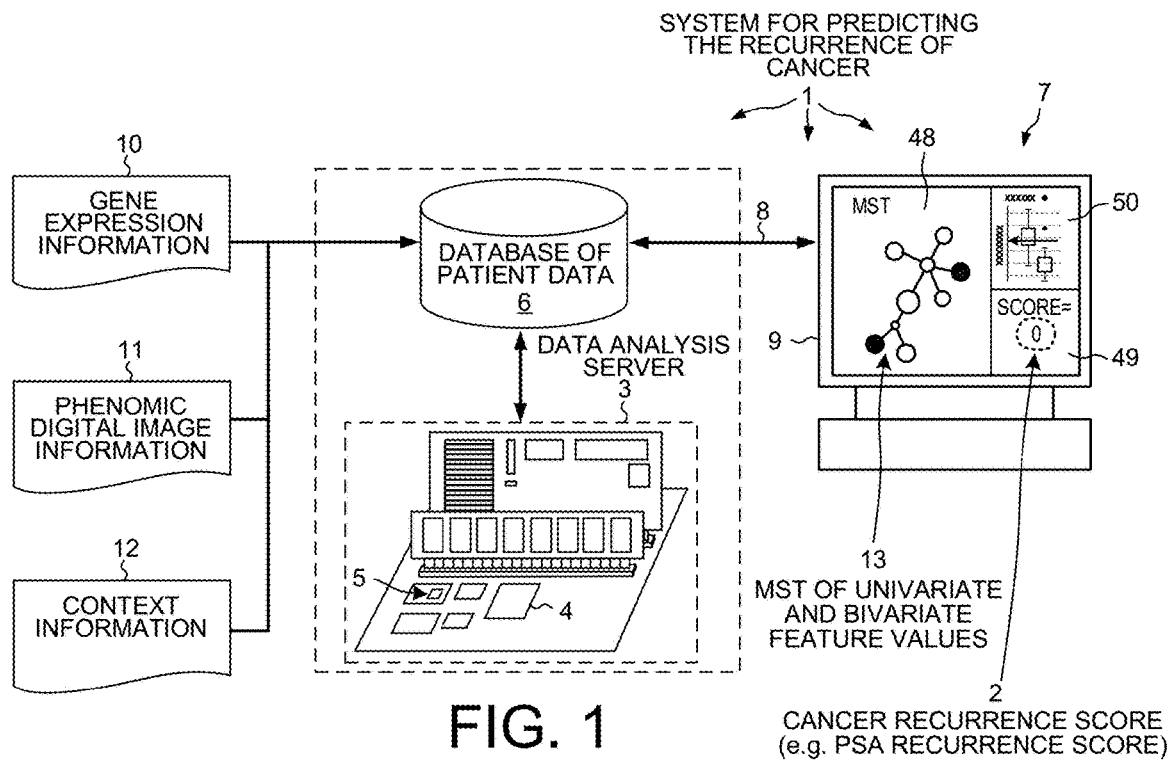
FIG. 1 is a diagram of a system for predicting the recurrence of cancer.

FIG. 1 is a conceptual diagram of a system 1 for predicting cancer recurrence using a prognostic method that analyzes genomic univariate features, as well as phenomic univariate features, as well as bivariate features of the two (of a genomic feature and a phenomic feature), and based at least in part on that analysis outputs a score 2. The score 2 is indicative of whether a patient will suffer a recurrence of cancer. System 1 includes a data analysis server 3. The server 3 has a processor 4 that executes system software 5. The software 5 is stored on the server 3 in a non-transitory processor-readable medium, such as semiconductor memory and/or magnetic disk storage. The server 3 also maintains, and/or provides access to, a database 6 of patient data. The database 6 may be stored on the server 3, or it may be stored remotely such that it is accessible to the server 3. The system 1 further includes a computer 7. The computer 7 is coupled to the server 3, for example by one or more networks or network connections 8. Computer 7 includes a keyboard (not shown) and a display 9. A user of the system 1 uses the computer 7 to enter information into the system. Information that the user can enter includes genomic feature information 10, phenomic feature information 11, and context information 12. The genomic feature information can be a set of counts, where each count indicates the degree of expression of a corresponding gene in the tissue of a cancer patient. The phenomic feature information 11 can be digital images taken of tissue of the cancer patient. In addition to this genomic and phenomic information about a patient, context information 12 for the patient is also loaded into the database 6. The context information 12 for a patient includes information about the patient including clinical cancer recurrence data. For each patient of a plurality of patients, the system user uses computer 7 to cause genomic information, phenomic information, and context information to be loaded into the system so that the information is stored in the database 6. In addition to the patients mentioned above, there is also a patient who is being seen in the clinical setting. It is for this patient that the score 2 is to be generated. The system user uses the computer 7 to cause both genomic and phenomic information about this patient to be loaded into the system 1 and to be stored in the database 6.

The system user uses computer 7 to interact with the system, and to view information served to the system user by server 3. The server 3 may cause this information to be displayed for viewing on the display 9 of the computer 7. An example of information that can be viewed is a Minimum Spanning Tree (MST) 13 of univariate features and bivariate features, where nodes (bubbles) of the MST represent univariate features, and where edges (interconnecting lines and arrows) of the MST represent bivariate features. The system 1, by virtue of processor 4 executing the system software 5, analyzes the genomic gene expression information and the phenomic digital image information along with the context information, and generates therefrom the score 2. The system 1 then causes the score 2 to be displayed on the display 9 of the computer 7.

What are referred to here as "phenomic features" are physical structural characteristics of features of tissue that are obtained by analyzing digital images of tissue. One or more slices of tissue are stained with one or more protein-specific immunohistochemical (IHC) stains. Such a stain is typically an antibody stain that has a fluorescent tag, where the antibody can bind to a particular target protein. The selective staining of different proteins is usable to reveal certain physical structures within the tissue. One or more digital images are taken of the stained tissue. One particular physical structural characteristic may, for example, be a count of certain types of structures within the tissue, or may be a size of those structures within the tissue, or may be a density of those structures within the tissue. A relationship between such detected structures in the tissue may also be considered to be a phenomic feature. One illustrative example of a relationship between detected structures is an average of distances between different types of structures detected within the tissue. Another example of a relationship between detected structures is a ratio of the number of one type of structure to another type of structure.

One example of a phenomic feature is the number of M1 macrophages in parts of tissue referred to as "influence zones". Another example of a phenomic feature is the number of M1 macrophages in other parts of tissue referred to as "stroma regions". Another example of a phenomic feature is the density of M2 macrophages in other regions of the tissue. Another example of a phenomic feature is a number that in turn is a function of multiple other such phenomic feature numbers. For detailed information on how tissue sample slices may be prepared, and stained with IHC stains, and imaged, and analyzed using image analysis in order to identify and to measure and to quantify phenomic features present in tissue of a cancer patient, see U.S. patent application Ser. No. 15/075,180, entitled "System for Predicting the Recurrence of Cancer in a Cancer Patient", filed Mar. 20, 2016, by Natalie Harder et al. (the entire subject matter of which is incorporated herein by reference).

One particular phenomic feature that is of particular interest in the prognostic method carried out by the system 1 of FIG. 1 is an average distance. This phenomic feature is referred to as "IHC_Dist_CD163(+)_CD3(+)CD8(−)". IHC-based staining and image analysis are used to identify CD163(+) stained objects in a tissue sample. These objects correspond to M2-type macrophages. IHC-based staining and image analysis is also used to identify CD3(+)CD8(−) objects in the same tissue sample. These objects correspond to non-cytotoxic T-cells in the tissue sample. Each CD163(+) object is then considered, and for that CD163(+) object the average distance (in micrometers) between it and the four nearest identified CD3(+)CD8(−) objects is determined. The average of all these averages for all the CD163(+) objects in the tissue sample is then determined, and this overall average is the raw measurement value for the IHC_Dist_CD163(+)_CD3(+)CD8(−) feature. Additional detail on how this raw measurement value is determined is set forth below.

In addition to analyzing "phenomic features", the system 1 of FIG. 1 also analyzes "genomic features". A "genomic feature", as that term is used here, is a characteristic of a particular DNA nucleotide sequence that is present in a tissue sample. This characteristic may be given as a count, where the count is indicative of the degree of expression of a particular gene present in the sample. Commercially available gene-specific biomarker probes exist that are designed so that they only attach to particular DNA nucleotide sequences, such as the nucleotide sequences that are present in parts of mRNA strands. In one example, a lysing buffer is used to lyse tissue to be analyzed into its constituent genetic material. The constituent genetic material is put into a solution. A pair of these biomarker "probes" is then mixed in. One of the probes is a capture probe that is selective in that it only attaches to a particular sequence of DNA nucleotides of a target molecule (for example, a target mRNA strand that includes the particular sequence of nucleotides). This capture probe can be made specific to particular DNA nucleotide subsequence found on a gene. The other probe of the probe pair is the reporter probe. This reporter probe has a color-coded barcode that can be illuminated and optically examined to identify it. In one example, a device called nCounter is used. The nCounter device is commercially available from NanoString Technologies, Inc., of Seattle, Wash. The nCounter device has a high-resolution CCD camera. The nCounter device is usable to illuminate the bar-code on each reporter probe, and thereby to determine the barcode of the probe and to count the number of times that a probe with that same particular barcode was detected in a tissue sample. The pair of probes is therefore said to be "gene-specific" in that the probe pair is usable as a biomarker for a specific gene that includes the particular sequence of DNA nucleotides for which the capture probe is selective. Gene-specific probe pairs are commercially available from multiple sources, including from NanoString Technologies, Inc. After the pair of probes has been mixed into the solution of genetic material and after the probes have attached to their target molecules, excess probes (unattached probes) in the solution are removed. The remaining probe/target complexes are then aligned and immobilized. The nCoutner device illuminates the probe/target complexes and uses its high-resolution CCD camera to perform optical examination of the probes. In this way, the probe on each individual target molecule is identified by its barcode to be a probe of a particular type, and the count of this particular probe type is incremented. After all the probes in the sample have been detected and counted in this way, the nCounter device outputs a digital file. Such a digital file is an example of the genomic information 10 (gene expression information 10) that is loaded into the system 1 of FIG. 1. This digital file includes a count value. The count value indicates the number of times that a probe of a particular type (bearing a particular color-coded barcode) was detected in the sample. The so-called "expression level" of a gene is a measurement of how large the count value is for the barcode of the probe that is specific to the gene of interest.

Although the nCounter device may involve a CCD camera and may perform optical inspections in order to identify probes, the nCounter is not doing wide-field phenomic image analysis in that it is not performing any analysis to identify cells, or particular types of cells, or groups of cells, or structural aspects of non-lysed tissue. The nCounter device is not measuring or outputting raw phenomic feature data. The term "phenomic" as it is used here is intended to exclude the data that results from the optical identification of gene-specific probes.

In a specific example of the prognostic method carried out by the system 1 of FIG. 1, there are two probe pairs that are of particular interest. The first probe pair is usable with the nCounter device to measure the gene expression of the LGALS3 gene. The LGALS3 gene is located in chromosome 14, locus q21-q22. The second probe pair is usable with the nCounter device to measure the expression of the MAGEC2 gene. The MAGEC2 gene is located in chromosome Xq27.2.

The prognostic method carried out by the system 1 of FIG. 1 has a "learning phase" and a "diagnostic phase". In the learning phase, both genomic feature information as well as phenomic feature information from each patient of a plurality of patients is generated, and then analyzed by the system. For each of these patients, information on many different genomic features and on many different phenomic features are typically collected and loaded into the system. The result of the learning phase is that the system 1 has information that is usable to generate a score 2 for a particular new patient in the later "diagnostic phase". This score 2 can be generated for the new patient without having to load but a small amount of genomic feature information and but a small amount of phenomic feature information for the new patient. Based on this relatively small amount of information, the system 1 can generate the score 2. The score 2 indicates whether the new patient will likely suffer cancer recurrence.

Figure 2:
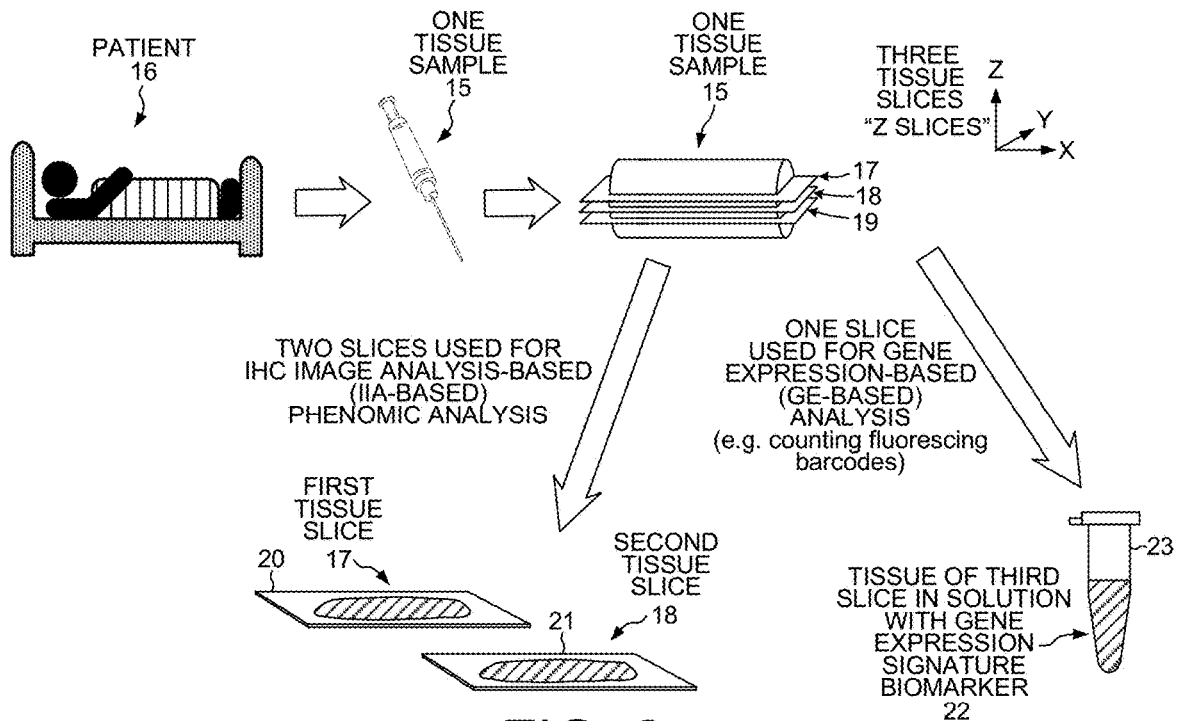
FIG. 2 is a diagram that illustrates how, in a "diagnostic phase" operation of the system of FIG. 1, a tissue sample from a patient is used to generate both raw phenomic feature measurement data as well as raw genomic feature measurement data.

FIG. 2 is a diagram that illustrates the "diagnostic phase" operation of the system 1. A tissue sample 15 is obtained (for example, by biopsy) from the new patient 16. The new patient 16 is the patient for whom the score 2 is to be generated. The tissue sample 15 is then sliced into very thin slices. Some of the slices are used to generate phenomic digital image information 11 that is supplied to the system 1 in the diagnostic phase for the new patient. Others of the slices are used to generate gene expression information 10 that is supplied to the system in the diagnostic phase for the new patient. In the illustration of FIG. 2, the first tissue slice 17 is stained with first pair of IHC stains and is put on a first slide 20. A first high-resolution color digital image of the slice 17 is taken and is supplied as first digital image information to the system. The second tissue slice 18 is stained with another pair of IHC stains and is put on a second slide 21. A second high-resolution color digital image of the slice 18 is taken and is supplied as second digital image information to the system. The digital image information derived from slices 17 and 18 is the raw measurement data used by the system 1 to generate a raw measurement value for the phenomic univariate feature for the new patient. The third tissue slice 19 is used for gene expression-based genomic analysis. The tissue of the third slice 19 is lysed and a first gene-specific probe pair for a first gene is attached, and a second gene-specific probe pair for a second gene is attached. In the specific example set forth below, the first gene is the LGALS3 gene and the second gene is the MAGEC2 gene. The resulting material 22 in the sample capsule 23 is processed by the nCounter device mentioned above, thereby generating a first count indicative of the degree of gene expression of the first gene, and a second count indicative of the degree of gene expression of the second gene. A digital computer file that records these counts is output from the nCounter device and is supplied to the system 1 of FIG. 1 as the gene expression information 10. These counts, as they are recorded in the digital file, are the raw measurement values for the genomic univariate features for the new patient. As is explained in further detail below, the system 1 generates a phenomic univariate feature score value (using the digital image information from the first and second digital images), generates a pair of genomic univariate feature score values (using the count data as output by the nCounter device), and further generates a pair of bivariate feature score values (each bivariate score value is based on both phenomic feature information and on genomic feature information). Based at least in part on these three univariate feature score values and on these two bivariate feature score values, the system 1 generates the overall score 2. The overall score 2 is then displayed on the display 9 of the computer 5.

The "learning phase" of the prognostic method is explained in further detail below by way of an example. In the example, there are twenty-three patients from whom a substantial amount of genomic information and a substantial amount of phenomic information is collected in the learning phase. For each of these twenty-three patients, the clinical cancer recurrence of the patient is known. Namely, whether the patient actually suffered a recurrence of cancer is known and this information is stored as part of the context information for the patient. In addition, if the patient did suffer such recurrence, then the date of that recurrence is known. This information is also stored as part of the context information 12 for the patient.

From each one of these twenty-three patients, a tissue sample is obtained. The resulting tissue sample block is sliced into numerous tissue slices. Some of these tissue slices are used to make raw measurements of various different phenomic univariate features. Information on many different phenomic univariate features is obtained. Others of the tissue slices are used to make raw measurements of various different genomic univariate features. Many different gene-specific probe pairs are employed to obtain gene expression information for many different genes. For a given feature, all the raw measurements for that feature are normalized. One normalization method that can be used is rank percentage normalization. It involves sorting the raw measurement values of the feature from smallest to largest, and then replacing each raw measurement value by a corresponding rank value equal to: (position in_the sorted_list−1)/(number_of samples−1). Then, using these normalized rank values, as well as the known clinical cancer recurrence information for the corresponding patients, a Kaplan-Meier plot analysis is performed for every possible cut-point within a quantile range of 40% to 60%. This results in a Kaplan-Meier log-rank test p-value for every cut-point. The −log of each p-value is determined, thereby generating a set of −log-p-values. A univariate feature that has a mean of these −log-p-values greater than $-\log_{10}(0.05)$ is considered to be prognostic. The cut-point having the largest −log-p-value is determined to be the cut-point for the univariate feature, and univariate feature value is the −log-p-value determined for that cut-point.

Next, the normalized rank values for each significant univariate feature are combined with the normalized rank values of each other significant univariate feature in order to calculate a bivariate feature value (a "−log(p-value)" for the bivariate feature). To combine a first feature (denoted f1) with a second feature (denoted C) in order to obtain a single (potentially prognostic) bivariate feature (denoted f12), four fuzzy logical combinations of the corresponding rank values of the two features are calculated. Those four fuzzy logical combinations are: 1) f12=f1*f2 (denoted "f1 and f2" of "SM1"); 2) f12=(1−f1)*f2 (denoted "not f1 and f2" or "SM2"); 3) f12=f1*(1−f2) (denoted "f1 and not f2" or "SM3"); and 4) f12=(1−f1)*(1−f2) (denoted "not f1 and not f2" or "SM4"). The determination of which fuzzy logical combination is considered significant is the same as the selection of significant univariate features as described above, except that here the determination of the significant bivariate features has the additional requirement that the log-rank-test p-value of the combination f12 must be at least a factor of ten times smaller than the smallest log-rank-test p-value from the univariate analysis of f1 or f2. For each bivariate feature, one of the four possible fuzzy logical combinations is determined to be the most significant, and the −log(p-value) of that combination is determined to be the bivariate feature value (the −log(p-value) for the bivariate feature).

To reduce the number of prognostic features by another step, the univariate feature values and the bivariate feature values as determined above are fashioned into a network (into a graph). The determined univariate feature values (−log(p-values)) are the bubbles (nodes) of the network. The determined bivariate feature values (−log(p-values)) are the arrows (edges) of the network.

A modified version of Prim's algorithm is then used to trim the network and thereby to obtain an extended Minimal Spanning Tree (MST). In this version of Prim's algorithm, all significant bivariate features are first sorted into descending order according to their −log(p-values). The most significant bivariate feature is then selected (first in the sorted list) to be a starting node of the MST. Then the bivariate feature list is iterated from top to end, and any bivariate feature f12 is added to the MST if at least f1 or f2 is not yet part of the MST. Additionally, f12 bivariate features are added if they are part of the top 75% quantile of all bivariate features. Any univariate features representing a bubble at an end of a bivariate feature in the tree, that is not present in the tree, is added to the tree. A tree layout method is then used to render a diagram of the extended MST. In one example, the open source graph visualization software tool called "Graphviz sfdp" is used to generate a visual rendering of the MST. The user of the system 1 of FIG. 1 can use the computer 7 to cause the rendered extended MST diagram to be displayed on the display 9 as shown in simplified form in FIG. 1.

Figure 3:
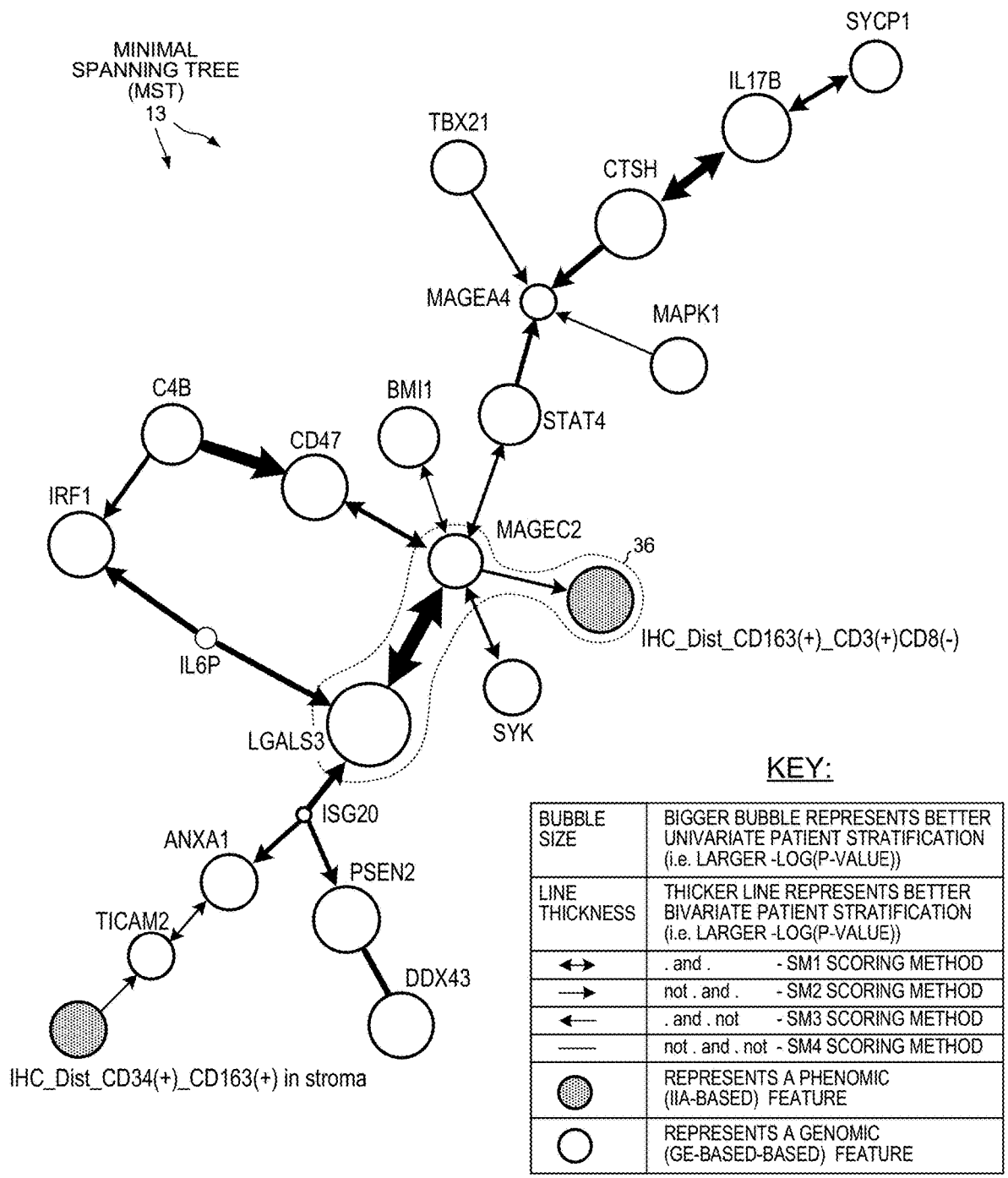
FIG. 3 is a diagram of a Minimal Spanning Tree (MST) that includes univariate phenomic features, univariate genomic features, and bivariate features. One of the bivariate features represents a relationship between a univariate phenomic feature and a univariate genomic feature.

FIG. 3 is a diagram of the extended MST 13 as it is rendered on display 9 of the computer 7. In the diagram, there is a bubble (node) for each univariate feature. The size of the bubble (node) indicates the prognostic significance of the univariate feature, namely a larger bubble indicates a larger −log(p-value), whereas a smaller bubble indicates a smaller −log(p-value). The larger the bubble, the more significant the univariate feature. In the diagram, a genomic univariate feature is denoted by its corresponding bubble being unshaded, whereas a phenomic univariate feature is denoted by its corresponding bubble being shaded. Genomic univariate features are displayed so that they can be visually distinguished from phenomic univariate features. In the diagram, the thickness of the arrow (edge) representing a bivariate feature indicates the prognostic significance of the bivariate feature, namely a thicker line represents a larger bivariate feature value (−log(p-value) for the bivariate feature), whereas a thinner line represents a smaller bivariate feature value (−log(p-value) for the bivariate feature). The thicker the line, the more prognostic significance the bivariate feature has. For each bivariate feature shown, the extended MST indicates which one of the four fuzzy logic combinations it was that was considered to be the most significant. As indicated by the key at the lower right of FIG. 3, the lack of an arrow head where an edge reaches a bubble indicates a "not" of the univariate feature represented by the bubble. A bivariate prognostic feature is considered to have significant prognostic value if the Kaplan-Meier p-value for the cohort of patients using the bivariate prognostic feature and a selected cut-point is less than 5%.

Figure 4:
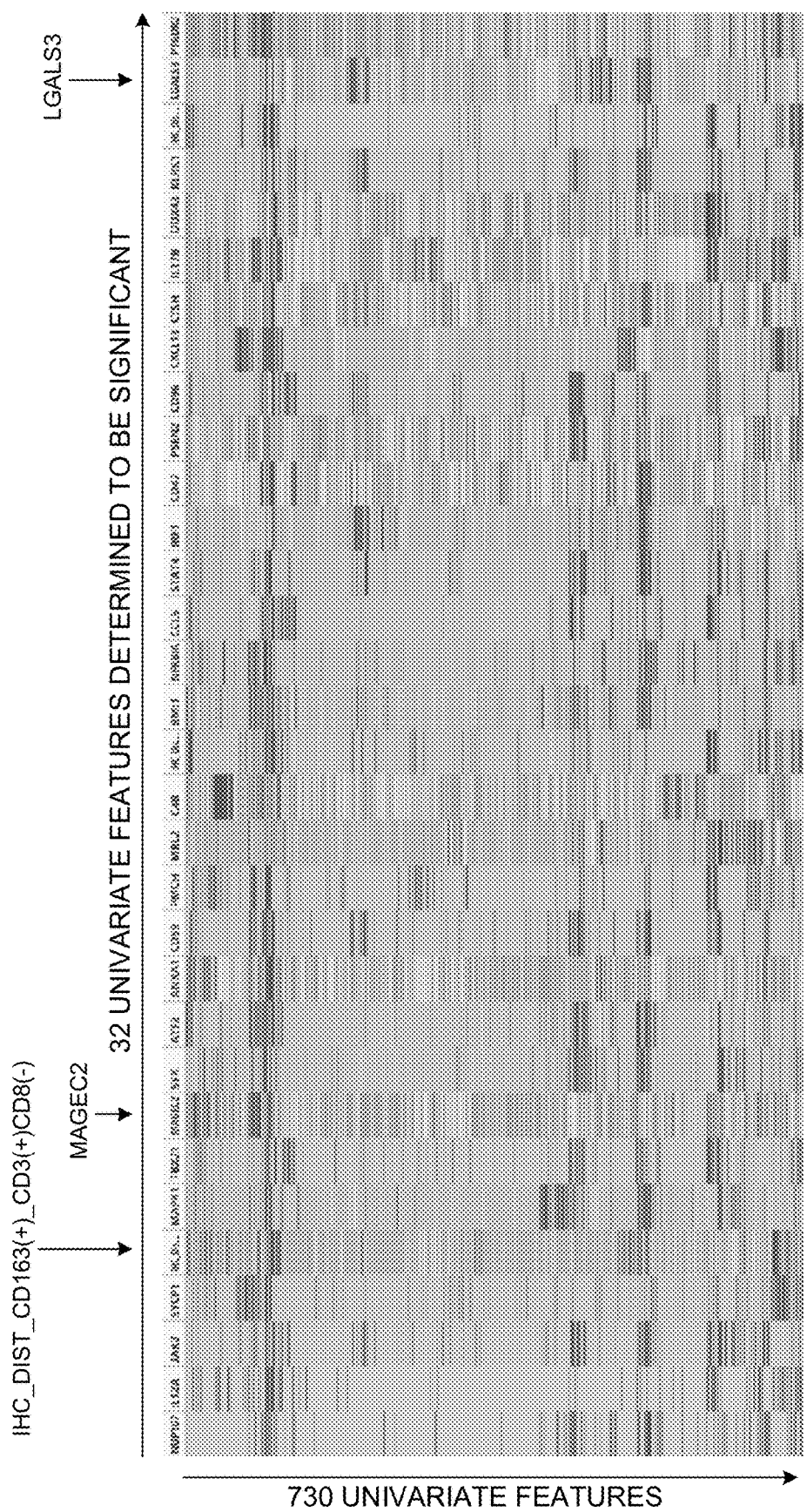
FIG. 4 is a two-dimensional matrix of the prognostic values (−log(log-rank p-values)) of bivariate relationships between various pairs of univariate features.

FIG. 4 is a portion of a two-dimensional matrix of the bivariate feature values. A bivariate feature value here is the −log(p-value) for the bivariate feature. The univariate features (including both phenomic and genomic features) that are determined to be significant are listed across the top of the matrix. Note that there is a column for the phenomic feature "IHC_Dist_CD163(+)_CD3(+)CD8(−)", and there is a column for the genomic feature "MAGEC2", and there is a column for the genomic feature "LGALS3". For each of the univariate features, there is also a corresponding row in the matrix. In this example, 730 univariate features were measuring in the learning phase, so there is one row in the matrix for each of the 730 univariate features. The thin rectangular intersection block of the matrix that appears in the column of one univariate feature and in the row of another univariate feature is shaded with a color. The darker the color of the intersection block of a bivariate feature, the more significant the bivariate feature is. Using the method described above, the most significant bivariate features are determined.

FIG. 5 is a table that sets forth the thirty-two univariate features that are determined to be most significant. A feature was determined to be significant if it had a significant (p<0.05) mean Kaplan Meier log-rank test p-value within a range of five cut-points.

Figure 6:
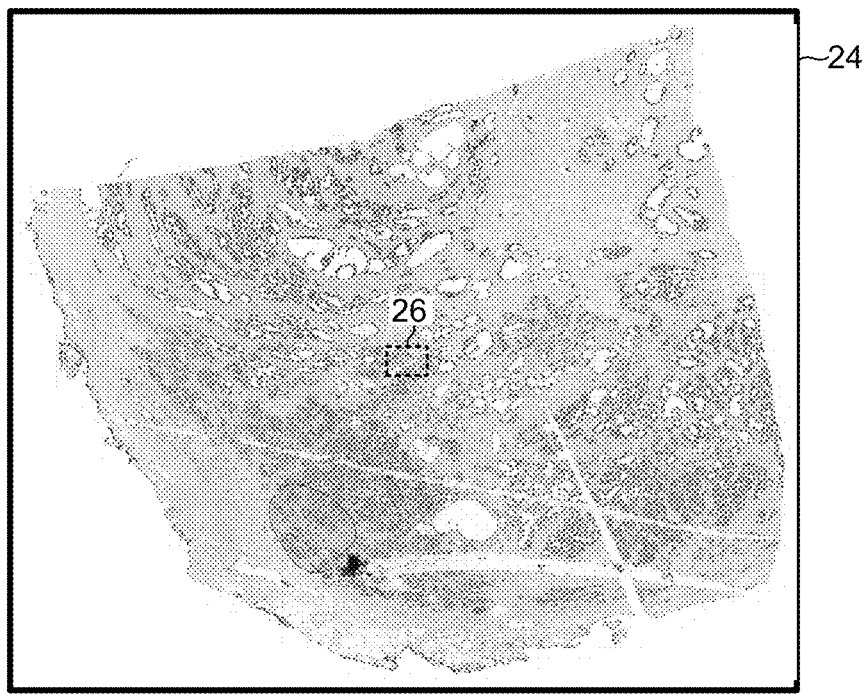
FIG. 6 is a grayscale version of a high-resolution digital image of a first slice of tissue that was duplex stained in an IHC-based image analysis process.

FIGS. 6-10 set forth more detail about how the "IHC_Dist_CD163(+)_CD3(+)CD8(−)" phenomic feature raw measurement data is obtained. Two consecutive tissue slices of the same tissue sample are stained with IHC-based stains in different ways. The first tissue slice is duplex-stained with a CD68 antibody stain and a CD163 antibody stain. The CD68 stain may, for example, be a stain referred to as #M087601- 2, available from Dako North America, Inc., 6392 Via Real, Carpinteria, Calif. 93013. The CD1623 stain may, for example, be a stain referred to as #760-4437, available from Ventana Medical Systems, Inc., 1910 Innovation Park Drive, Tucson, Ariz. 85755. Due to this double staining, individual tumoricidal M1 type macrophages appear red when the slice is viewed under magnification, and individual tumorigenic M2 type macrophages appear brown when the slice is viewed under magnification. After staining, the slice is placed on a slide. A high-resolution color digital image 24 is then taken of the stained slice. FIG. 6 is a grayscale version of the high-resolution digital image 24.

Figure 7:
FIG. 7 is a grayscale version of a high-resolution digital image of a second slice of tissue that was duplex stained in the IHC-based image analysis process.

The second tissue slice is also duplex stained, but this slice is stained with a CD3 antibody stain and a CD8 antibody stain. Due to this double staining, individual non-cytotoxic T-cells appear red when the slice is viewed under magnification, and individual cytotoxic T-cells appear brown when the slice is viewed under magnification. After staining, the slice is placed on a slide. A high-resolution color digital image 25 is then taken of the stained slice. FIG. 7 is a grayscale version of the high-resolution digital image 25.

Figure 8:
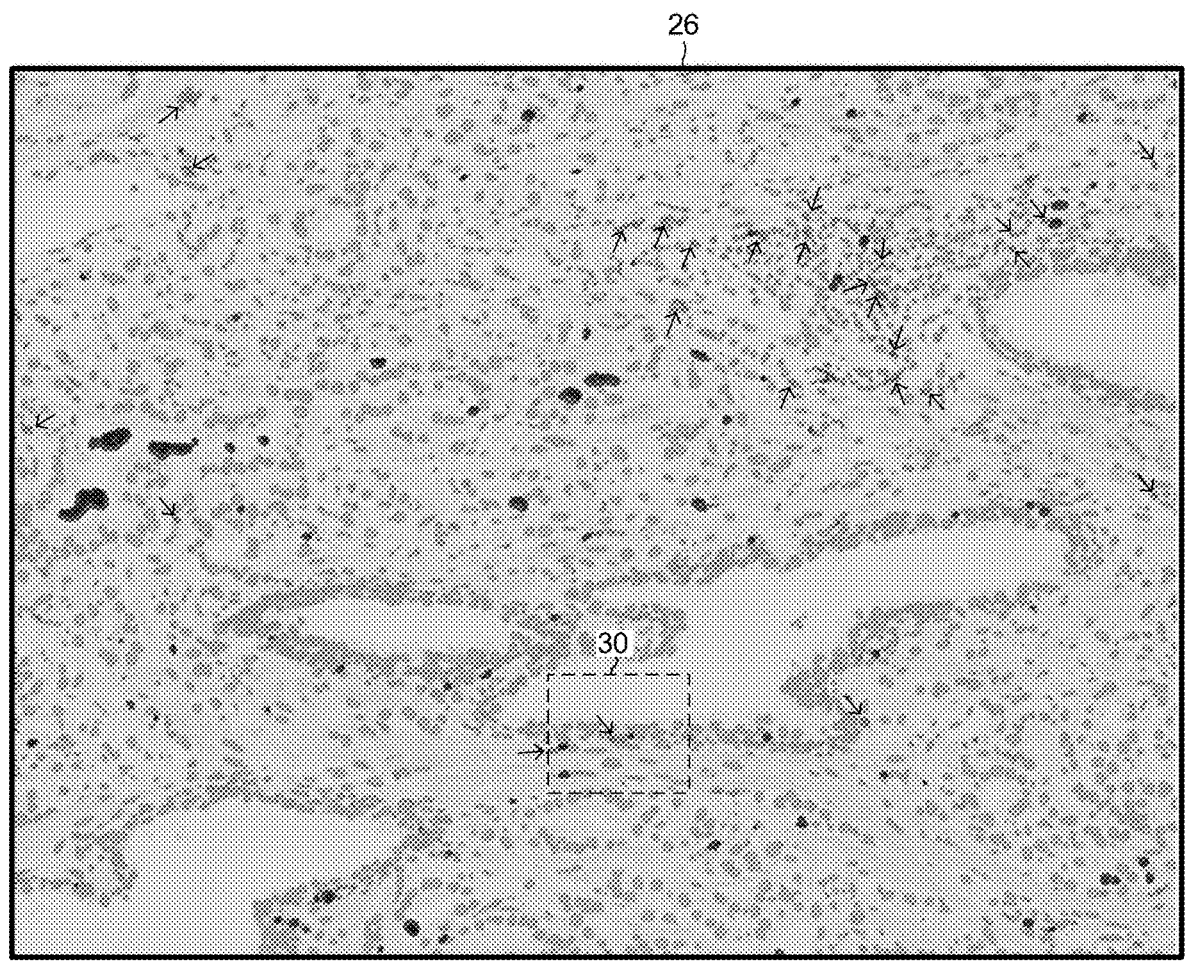
FIG. 8 is an expanded view of a portion of the first digital image of FIG. 6.

FIG. 8 is an expanded view of a portion 26 of the first digital image 24 of FIG. 6. The system 1 performs image analysis on the first digital image, thereby identifying CD163(+)-stained objects. The arrows in FIG. 8 identify the CD163(+)-stained objects. The location in the X-Y dimension of the center of each detected CD163(+) object is logged. The CD163(+)-stained objects of FIG. 8 correspond to M2 macrophages.

Figure 9:
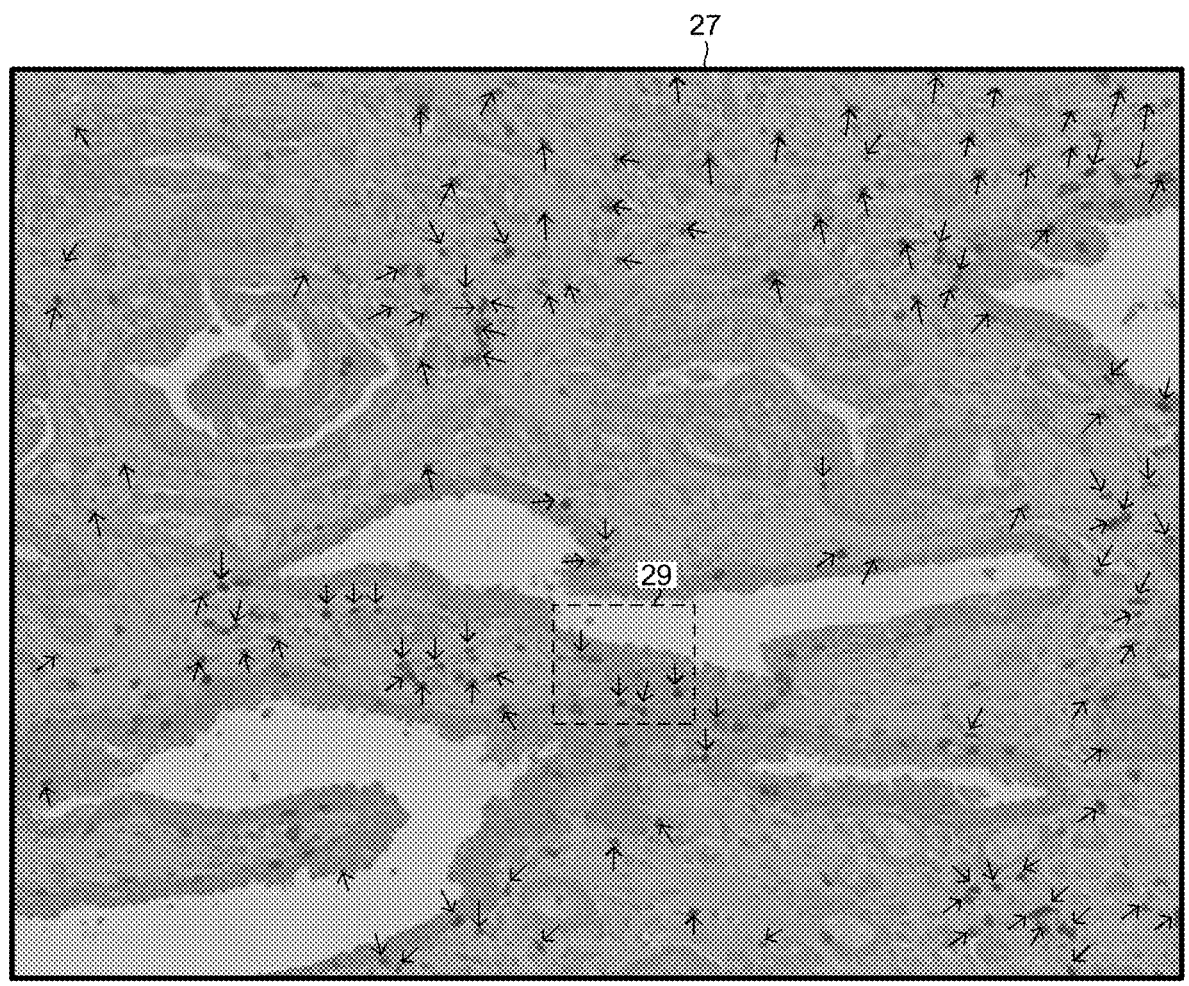
FIG. 9 is an expanded view of a portion of the second digital image of FIG. 7.

FIG. 9 is an expanded view of a portion 27 of the second digital image 25 of FIG. 7. The portion 27 of the second digital image 25 is same X-Y dimension as is the portion 26 of the first digital image 24. The tissue represented in the two portions 27 and 26 are, however, slightly offset in the Z dimension. The system 1 performs image analysis on the second digital image 25, thereby identifying CD3(+)CD8(−) objects. The arrows in FIG. 9 identify the identified CD3(+)CD8(−) objects. The location in the X-Y dimension of the center of each detected CD3(+)CD8(−) object is logged. Individual CD3(+)CD8(−) objects correspond to individual non-cytotoxic T-cells.

Figure 10:
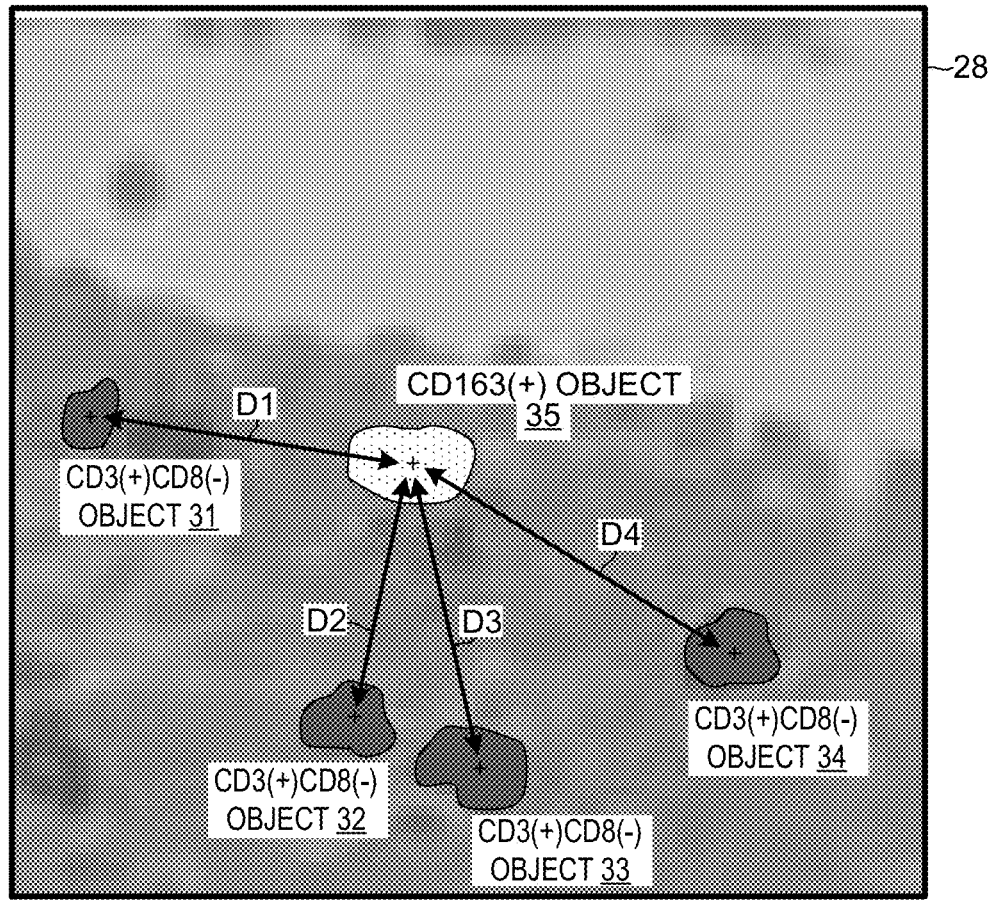
FIG. 10 is an illustrative diagram that shows how the average distance from a CD163(+) object to its nearest four CD3(+)CD8(−) objects is determined.

FIG. 10 is an illustrative diagram that shows how the average distance from a CD163(+) object to its nearest four CD3(+)CD8(−) objects is determined. The X-Y image block portion identified by reference numeral 28 in FIG. 10 represents the same X-Y block of tissue as does block 29 in FIG. 9 and as does block 30 in FIG. 8. The CD3(+)CD8(−) objects 31-34 are determined to be the four such objects that are the closest (in the X-Y dimension) to the CD163(+) object 35. The distances D1, D2, D3 and D4 are determined from the logged center locations of the CD3(+)CD8(−) objects 31-34 and the CD163(+) object 35. The average of the distances D1, D2, D3 and D4 in micrometers is determined and recorded. This process is repeated for all the CD163(+) object detected in the first digital image 24. All these averages are in turn averaged in order to obtain one overall average. This one overall average number (in units of micrometers) is the "IHC_Dist_CD163(+)_CD3(+)CD8(−)" phenomic feature raw measurement value for the patient from whom the first and second tissue slices were taken.

Inspection of the extended MST 13 of FIG. 3 indicates that a phenomic univariate feature can be advantageously used in the diagnostic phase along with two genomic univariate features, and along with two associated bivariate features, to generate the score 2. The dashed line 36 in FIG. 3 encircles these five features. The MST 13 is viewable by the system user during and after the learning phase so that the system user can review the results of the learning phase, and can identify the features that the learning phase identified as being significant. This information is usable to design a diagnostic clinical test (for example, a test to predict cancer recurrence) that is effective, and yet only employs a relatively small number of features.

FIGS. 11-37 are a sequence of diagrams that set forth how the raw measurement values for the three univariate features (the LGALS3 feature, the MAGEC2 feature, and the IHC_DIST_CD163(+)_CD3(+)CD8(−) feature) is processed in preparation for the "diagnostic phase".

FIG. 11 shows the LGALS3 raw measurement data values. As mentioned above, the LGALS3 feature is a genomic feature, so the listed raw measurement values are counts. For each patient of the twenty-three patients, there is a raw measurement count. The right column sets forth the known cancer recurrence information for the associated patient. For example, the patient identified with patient ID of "4" was known not to suffer cancer recurrence, so the indicated value is "No". The LGALS3 raw measurement count for this patient is "1159", as indicated by the corresponding entry for patient "4" in the middle column of the table.

FIG. 12 shows how the information in the rows of FIG. 11 is reordered (i.e., is "sorted") so that the top row is for the patient having the smallest raw measurement count, and so that the bottom row is for the patient having the largest raw measurement count.

Figures 13, 14:
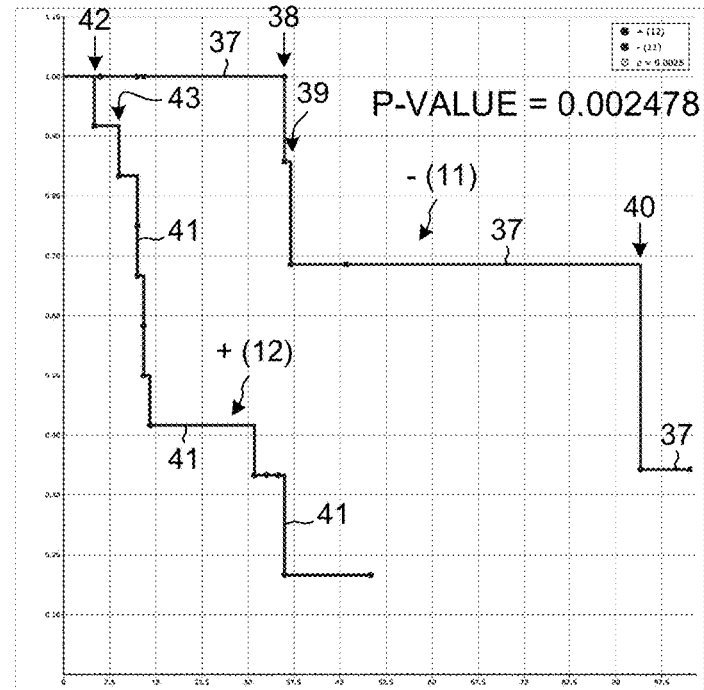
FIG. 13 shows how the raw measurement count values of FIG. 12 are normalized by rank percentage.
FIG. 14 is a Kaplan-Meier plot for the data of FIG. 13.

FIG. 13 shows how the raw measurement count values of FIG. 12 are then normalized into "rank normalized values". The smallest raw count value is replaced with the value 0/22, the next smallest raw count value is replaced with the value 1/22, and so forth. The denominator of the replacement values is the number of patients supplying the data (in this case, twenty-three) minus one. For the univariate features, a predetermined fixed cutpoint value of 0.499 repeating is used. Accordingly, there are eleven patients in the group of patients above the cut-point value, and there are twelve patients the group of patients below the cut-point value. The p-value for this grouping is calculated to be 0.002478.

FIG. 14 is a Kaplan-Meier plot for the LGALS3 data of FIG. 13. The horizontal axis represents time. The upper line 37 represents the group of eleven patients above the cut-point in FIG. 13. This group of patients is estimated by the grouping to be patients who will not suffer cancer recurrence. At the time indicated by arrow 38, however, one of these patients did suffer recurrence. The upper line 37 of the Kaplan-Meier plot therefore drops downward an amount to reflect the number of patients suffering recurrence at this time. Then later, at the time indicated by arrow 39, another of the patients in this group suffered recurrence. The upper line 37 therefore drops downward further. No more of the patients of this group suffered recurrence until the time indicated by arrow 40, at which point another patient suffered recurrence. The upper line 37 therefore drops downward at again. The lower line 41 represents the group of twelve patients below the cut-point in FIG. 13. This group of patients is estimated by the grouping to be patients who will suffer recurrence. None of the patients of this group suffered recurrence until the time indicated by arrow 42. At this time a patient in this second group suffered recurrence, so the bottom line 41 drops downward an amount to reflect the number of patients suffering recurrence at that time. Similarly, at the time indicated by arrow 43 another of the patents of this second group sufferance recurrence, and therefore the lower line 41 drops downward again. If the grouping of patients as reflected by the cut-point were perfect, then the upper line 37 would extend horizontally from left to right over time, without ever dropping, because none of the patients represented by that upper line 37 would ever have suffered cancer recurrence. As to the bottom line 41, by the end of time at that right of the plot, that bottom line 41 would reach the very bottom of the plot because all the patients of the second group as represented by the bottom line 41 would have suffered cancer recurrence at some time. The actual Kaplan-Meier plot for the predetermined 0.499 cut-point and patient grouping of FIG. 13 is shown in FIG. 14.

FIG. 15 shows the MAGEC2 raw measurement data values for the twenty-three patients being studied in the learning phase.

FIG. 16 shows the information in the rows of FIG. 15 in reordered form (i.e., "sorted") so that the top row is for the patient having the smallest raw measurement count, and so that the bottom row is for the patient having the largest raw measurement count.

Figures 17, 18:
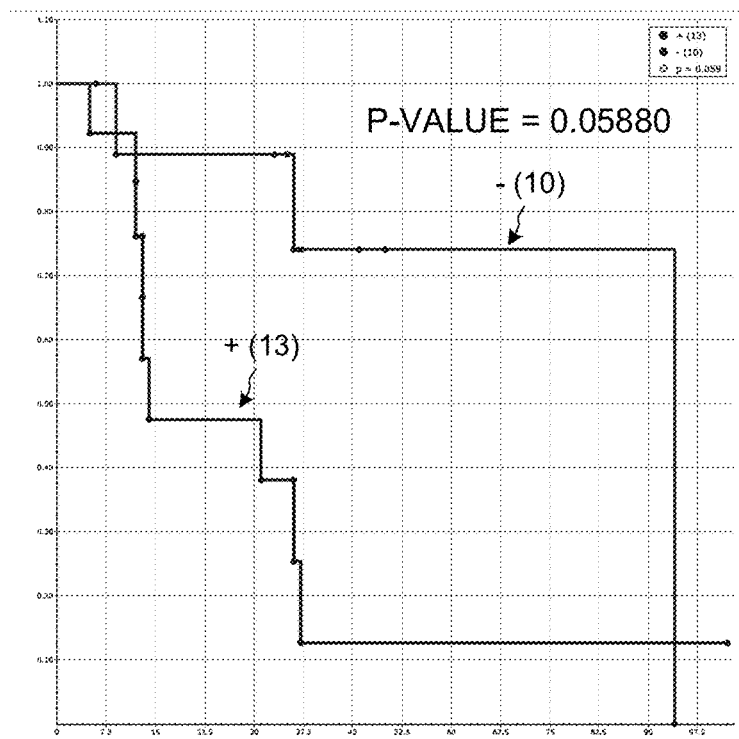
FIG. 17 shows how the raw measurement count values of FIG. 16 are normalized by rank percentage.
FIG. 18 is a Kaplan-Meier plot for the data of FIG. 17.

FIG. 17 shows how the ranked raw measurement count values of FIG. 16 are then normalized into rank normalized values. The cut-point value is the same predetermined cut-point value of 0.499 repeating as in FIG. 13.

FIG. 18 is a Kaplan-Meier plot for the MAGEC2 data of FIG. 17. For the predetermined cut-point value of 0.499 repeating as shown in FIG. 17, there are ten patients in a first group and there are thirteen patients in a second group. The p-value for this grouping is 0.05880.

FIG. 19 shows the IHC_DIST_CD163(+)_CD3(+)CD8 (−) raw measurement data values for the twenty-three patients being studied in the learning phase. These values are distances in micrometers.

FIG. 20 shows the information in the rows of FIG. 19 in reordered form (i.e., "sorted").

Figures 21, 22:
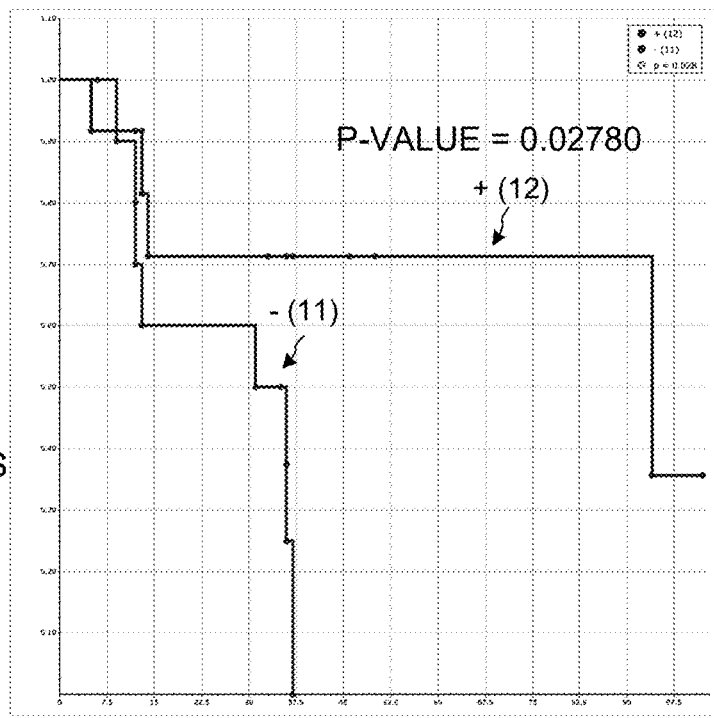
FIG. 21 shows how the raw measurement count values of FIG. 20 are normalized by rank percentage.
FIG. 22 is a Kaplan-Meier plot for the data of FIG. 21.

FIG. 21 shows how the ranked raw measurement count values of FIG. 20 are then normalized. The cut-point value is the same predetermined cut-point value of 0.499 repeating as in FIG. 17 and FIG. 13. The p-value for this grouping is 0.02780.

FIG. 22 is a Kaplan-Meier plot for the data of FIG. 21. For the predetermined cut-point value of 0.499 repeating as shown in FIG. 21, there are twelve patients in a first group and there are eleven patients in a second group. The p-value for this grouping is 0.02780.

FIG. 23 is a table that shows the four "fuzzy logic" bivariate scoring methods. These scoring methods are denoted SM1, SM2, SM3 and SM4.

FIG. 24 is a diagram that shows how LGALS3-to-MAGEC2 normalized rank values are calculated using the first bivariate scoring method SM1. The leftmost two columns of the diagram set forth the normalized rank values for LGALS3. These are the normalized LGALS3 values of FIG. 13, except that they have been reordered according to patient ID. The next two leftmost columns of the diagram set forth the normalized rank values for MAGEC2. These are the normalized MAGEC2 values of FIG. 17, except that they have been reordered according to patient ID. For each patient ID, the normalized value in the LGALS3 column for that patient ID is multiplied by the normalized value in the MAGEC2 column for that patient ID. The resulting values are indicated in the column denoted "f1×f2". The normalized LGALS3 value is simply multiplied by the normalized MAGEC2 value because the scoring method is SM1, and according to the table of FIG. 23, the f1 value for the patient is multiplied by the f2 value for patient K, where the variable K goes from one (for the patient having the patient ID of "1") to twenty-three (for the patient having the patient ID of "23"). The rows of the "f1×f2" column are then reordered (i.e., "sorted") so that the top row has the smallest "f1×f2" value, and so that the bottom row has the largest "f1×f2" value. For the predetermined cut-point at the median value of 0.2121, there is a first group of eleven patients, a second group of twelve patients. For this patient grouping, the corresponding p-value is 0.0009008.

FIG. 25 is a diagram that shows how the cut-point and p-value for the LGALS3-to-MAGEC2 bivariate relationship is determined when the second bivariate scoring method SM2 is used. The cut-point is predetermined to be the median value of 0.2273. The same process as set forth above in connection with FIG. 24 is performed, except that the "f1×f2" column of FIG. 24 is replaced with a "(1-f1)×f2" column. The values in this column are then reordered so that the smallest SM2 value is at the top of the reordered column, and so that the largest SM2 value is at the bottom of the reordered column. This reordered information is the rightmost column in FIG. 25 that is labeled "LGALS3-to-MAGEC2 normalized rank values for SM2". For the predetermined cut-point at the median value of 0.2273, there is a first group of eleven patients and a second group of twelve patients. For this patient grouping, the corresponding p-value is 0.9806.

FIG. 26 is a diagram that shows show how the cut-point and p-value for the LGALS3-to-MAGEC2 bivariate relationship is determined when the second bivariate scoring method SM3 is used. Again, the cut-point is predetermined to be the median value of 0.1515. For the predetermined cut-point at the median value of 0.1515, there is a first group of eleven patients and a second group of twelve patients. For this patient grouping, the corresponding p-value is 0.8034.

FIG. 27 is a diagram that shows show how the cut-point and p-value for the LGALS3-to-MAGEC2 bivariate relationship is determined when the second bivariate scoring method SM4 is used. Again, the cut-point is predetermined to be the median value of 0.2272. For the predetermined cut-point at the median value of 0.2272, there is a first group of eleven patients and a second group of twelve patients. For this patient grouping, the corresponding p-value is 0.006845.

Figures 28, 29:
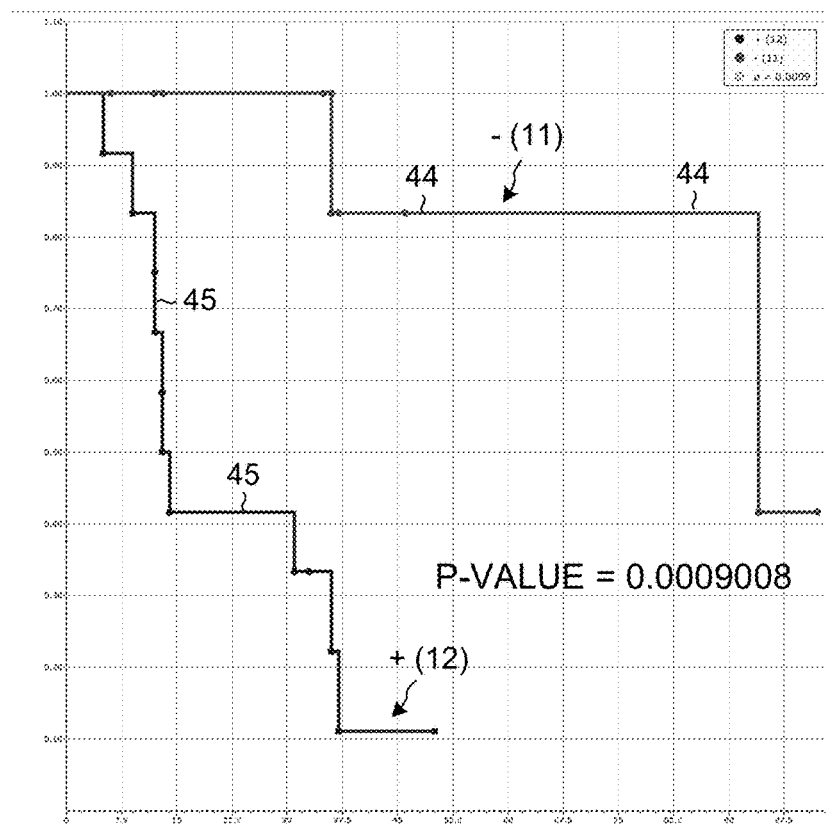
FIG. 28 is a table showing the p-values determined for the LGALS3-to-MAGEC2 bivariate relationship for each of the four scoring methods SM1, SM2, SM3 and SM4.
FIG. 29 is a Kaplan-Meier plot for the LGALS3-to-MAGEC2 bivariate relationship when the SM1 bivariate scoring method is used.

FIG. 28 is a table showing the p-values determined for the LGALS3-to-MAGEC2 bivariate relationship for each of the four scoring methods SM1, SM2, SM3 and SM4. Scoring method SM1 resulted in the smallest p-value, so scoring method SM1 is selected to be the scoring method used.

FIG. 29 is a Kaplan-Meier plot for the LGALS3-to-MAGEC2 bivariate relationship when the SM1 scoring method is used. As indicated by the diagram of FIG. 21 for the SM1 scoring method, the cut-point value of 0.2273 divides the patients into a first group of eleven patients and a second group of twelve patients. The first group is represented by the line 44 in the Kaplan-Meier plot of FIG. 29. The second group is represented by the line 45 in the Kaplan-Meier plot of FIG. 29.

The same process described above for the LGALS3-to-MAGEC2 bivariate relationship in connection with FIGS. 24-29 is performed for the IHC_Dist_CD163(+)_CD3(+)CD8(-)-to-MAGEC2 bivariate relationship. FIG. 30 shows how the cut-point value and the p-value for the SM1 scoring method are determined. The cut-point is predetermined to be the median value of 0.2121. FIG. 31 shows how the cut-point value and the p-value for the SM2 scoring method are determined. The cut-point is predetermined to be the median value of 0.1439. FIG. 32 shows how the cut-point value and the p-value for the SM3 scoring method are determined. The cut-point is predetermined to be the median value of 0.2121.

Figures 34, 35:
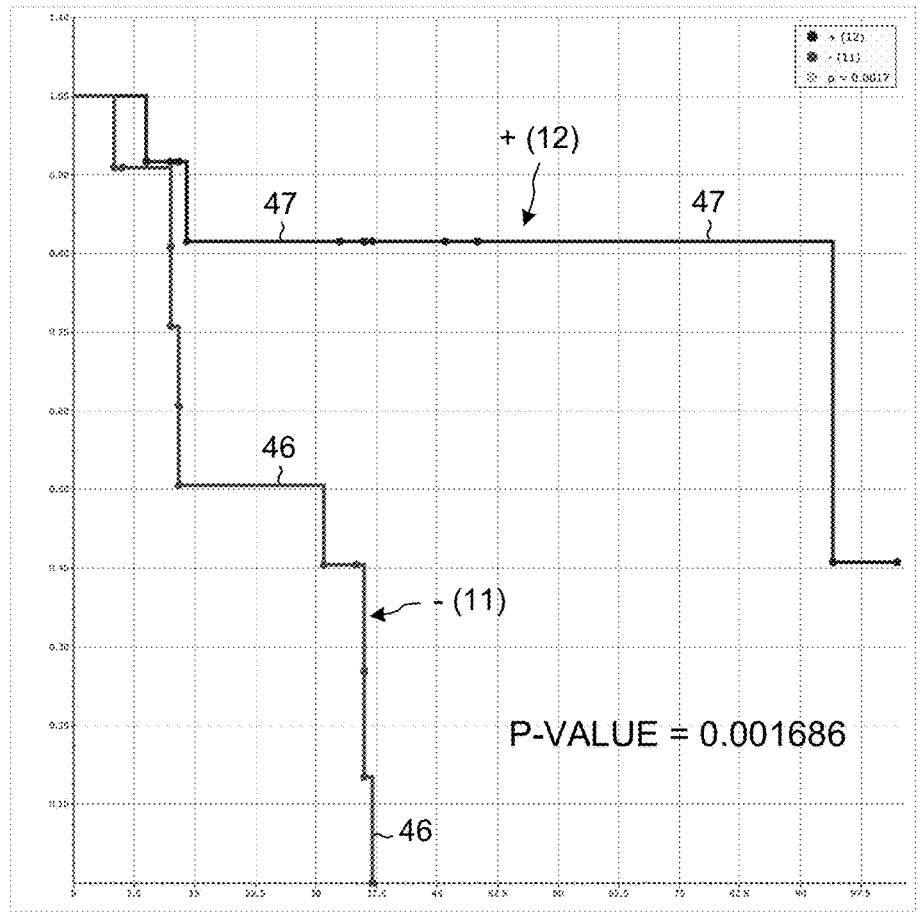
FIG. 34 is a table showing the p-values determined for IHC_DIST_CD163(+)_CD3(+)CD8(−)-to-MAGEC2 bivariate relationship for each of the four scoring methods SM1, SM2, SM3 and SM4.
FIG. 35 is a Kaplan-Meier plot for the IHC_DIST_CD163 (+)_CD3(+)CD8(−)-to-MAGEC2 bivariate relationship when the SM3 scoring method is used.

FIG. 33 shows how the cut-point value and the p-value for the SM4 scoring method are determined. The cut-point is predetermined to be the median value of 0.2386. FIG. 34 is a chart showing the p-values determined for each of the four scoring methods SM1, SM2, SM3 and SM4. The chart reveals that the smallest p-value is obtained when the SM3 scoring method is used. The SM3 scoring method is therefore determined to be the method used. FIG. 35 is a Kaplan-Meier plot for the IHC_Dist_CD163(+)_CD3(+)CD8(-)-to-MAGEC2 bivariate relationship when the SM3 scoring method is used. The predetermined median value cut-point of 0.2121 divides the twenty-three patients into a first group of eleven patients and a second group of twelve patients. The first group is represented by the line 46 in the Kaplan-Meier plot of FIG. 35. The second group is represented by the line 47 in the Kaplan-Meier plot of FIG. 35.

Accordingly, the "learning phase" results in the generation of both a cut-point value and a rank normalized value list for each of the three univariate features, and for each of the two bivariate features. This information is stored in the database 6 for later use in the diagnostic phase.

Operation of the system 1 of FIG. 1 in the "diagnostic phase" is described below in connection with FIGS. 36-43. The new patient for whom the score 2 is to be determined is seen in a clinical setting, and a tissue sample is obtained from the patient. The tissue sample is sliced and analyzed as explained above in connection with FIG. 2. The first and second tissue slices are stained and imaged and analyzed by the system so as to generate an IHC_Dist_CD163(+)_CD3(+)CD8(-)-to-MAGEC2 raw measurement value. The third tissue slice is lysed and two pairs of probes are applied. The nCounter device is used to count probes, thereby generating two count values. These two count values are loaded into the system as the LGALS3 raw measurement value and the MAGEC2 raw measurement value. The three raw measurement values for the new patient are set forth in FIG. 36.

Figures 36, 37:
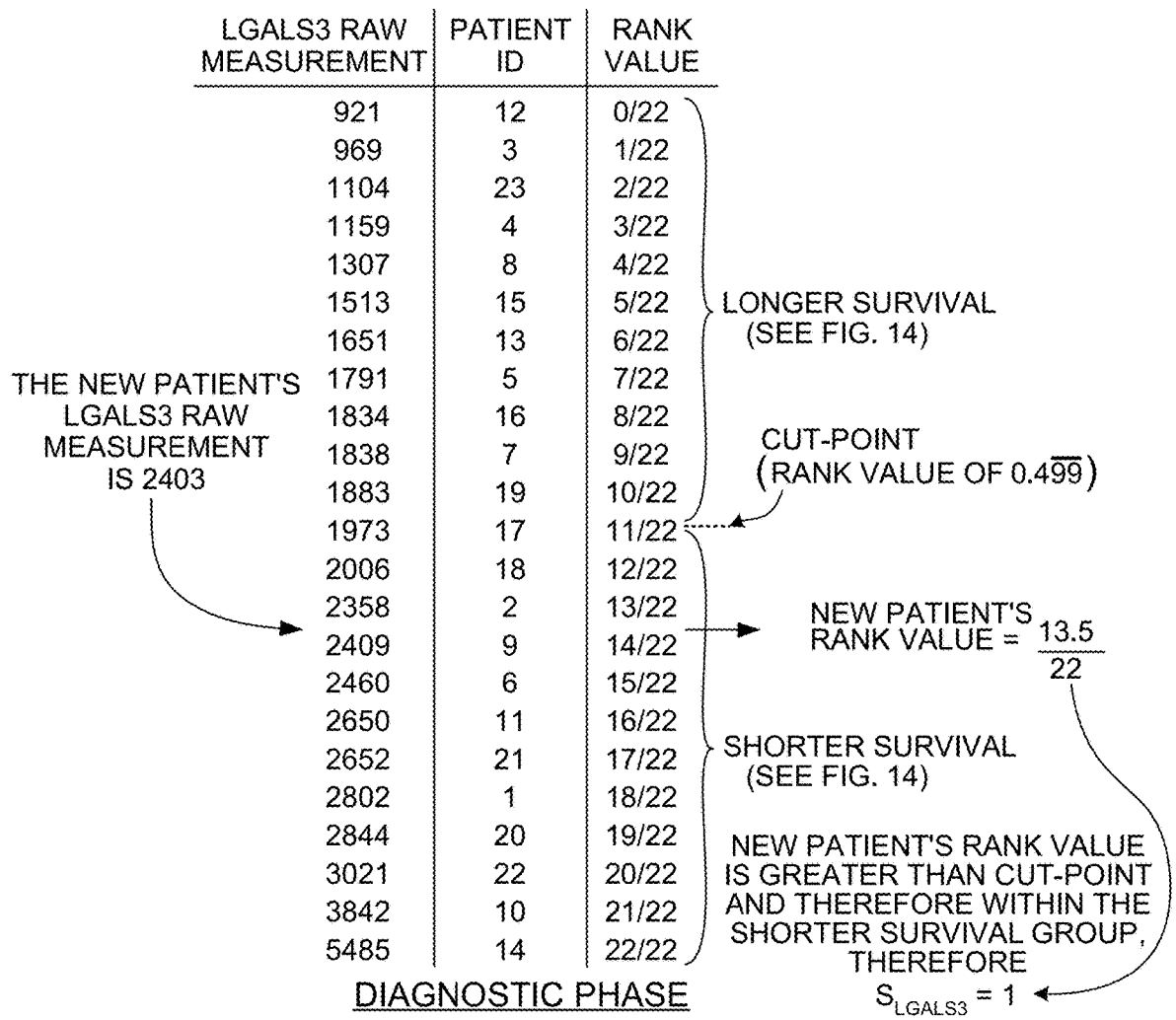
FIG. 36 is a table showing three raw measurement values for the new patient (to be used in the diagnostic phase to determine a score for the new patient).
FIG. 37 shows how a score value is determined in the diagnostic phase for the LGALS3 univariate feature.

FIG. 37 shows the ordered rank values, the corresponding LGALS3 raw measurement values, and the cut-point value of FIG. 13 as determined in the learning phase for the LGALS3 univariate feature. Patient rank values that are greater than the cut-point value are for patients in the shorter survival group, whereas patient rank values that are smaller than the cut-point value are for patients in the longer survival group. For each patient ID, the LGALS3 raw measurement value is listed. The LGALS3 raw measurement value of 2403 for the new patient is compared to this list of raw measurement values obtained in the learning phase. As illustrated in FIG. 37, the 2403 value for the new patient is a value between the 2358 value for patient number 2 and the 2409 value for patient number 9. A rank value for the raw score of the new patient is then determined. The rank value corresponding to the 2403 raw measurement value is between the rank value for patient number 2 (who has a raw measurement value of 2358) and patient number 9 (who has a raw measurement value of 2409). The rank value for the new patient must therefore be between the rank value of 13/22 for patient number 2 and the rank value of 14/22 for patient number 9. In the present example, because the rank value for the new patient is between these two values, a rank value for the new patient is determined in simplified fashion to be a rank value of 13.5/22 which is midway between the two rank values of 13/22 and 14/22. This rank value of 13.5/22. This rank value of 13.5/22 for LGALS3 is stored for later use in the determining a bivariate feature score. If the rank value for the new patient is greater than the cut-point value, then an LGALS3 univariate feature score $S_{LGALS3}$ has a value of "1", otherwise the score $S_{LGALS3}$ has a value of "0". In the case of the raw measurement value being 2403, the corresponding rank value of 13.5/22 is greater than the cut-point value of 0.499, so the $S_{LGALS3}$ score value is "1".

FIG. 38 shows the ordered rank values and the cut-point value determined in the learning phase for the MAGEC2 univariate feature. The same process described above in connection with LGALS3 and FIG. 37 is performed here for MAGEC2. The new patient's MAGEC2 raw measurement value of 5 points to a location in the list of raw MAGEC2 measurements that is above (smaller than) the raw measurement value of 6 for patient number 2. The rank value of the new patent is therefore determined to be 0/12. This rank value of 0/12 for MAGEC2 is stored for later use in the determining of bivariate feature scores. Because the rank value of 0/12 for the new patient is smaller than the cut-point value of 0.499, the rank value for the new patient is within the set of rank values for the "longer survival" group of patients. The $S_{MAGEC2}$ score value is therefore determined to be "0".

FIG. 39 shows the ordered rank values and the cut-point value determined in the learning phase for the IHC_Dist_CD163(+)_CD3(+)CD8(−) univariate feature. The same process described above in connection with LGALS3 and FIG. 37 is performed here for IHC_Dist_CD163(+)_CD3(+)CD8(−). The new patient's raw measurement value of 700 points to a location in the ordered list between patient number 9 and patient number 16. Patient number 9 has a rank value of 6/22 and patient number 16 has a rank value of 7/22, so the rank value for the new patient is determined to be rank value midway between these two values, namely 6./5/22. As can be seen from FIG. 39, rank values below the cut-point indicate relatively longer survival instances, as compared with rank value above the cut-point which indicate relatively shorter survival instances. In the case of the IHC_Dist_CD163(+)_CD3(+)CD8(−) univariate feature, therefore, being below (greater than) the cut-point value indicates relatively longer survival, whereas being above (smaller than) the cut-point value indicates relatively shorter survival. Because the new patient's raw measurement value of 700 corresponds to a rank value of 6.5/22, and because this rank value is smaller than the cut-point value of 0.499, the $S_{IHC}$ score value is determined to be "1".

Figure 40:
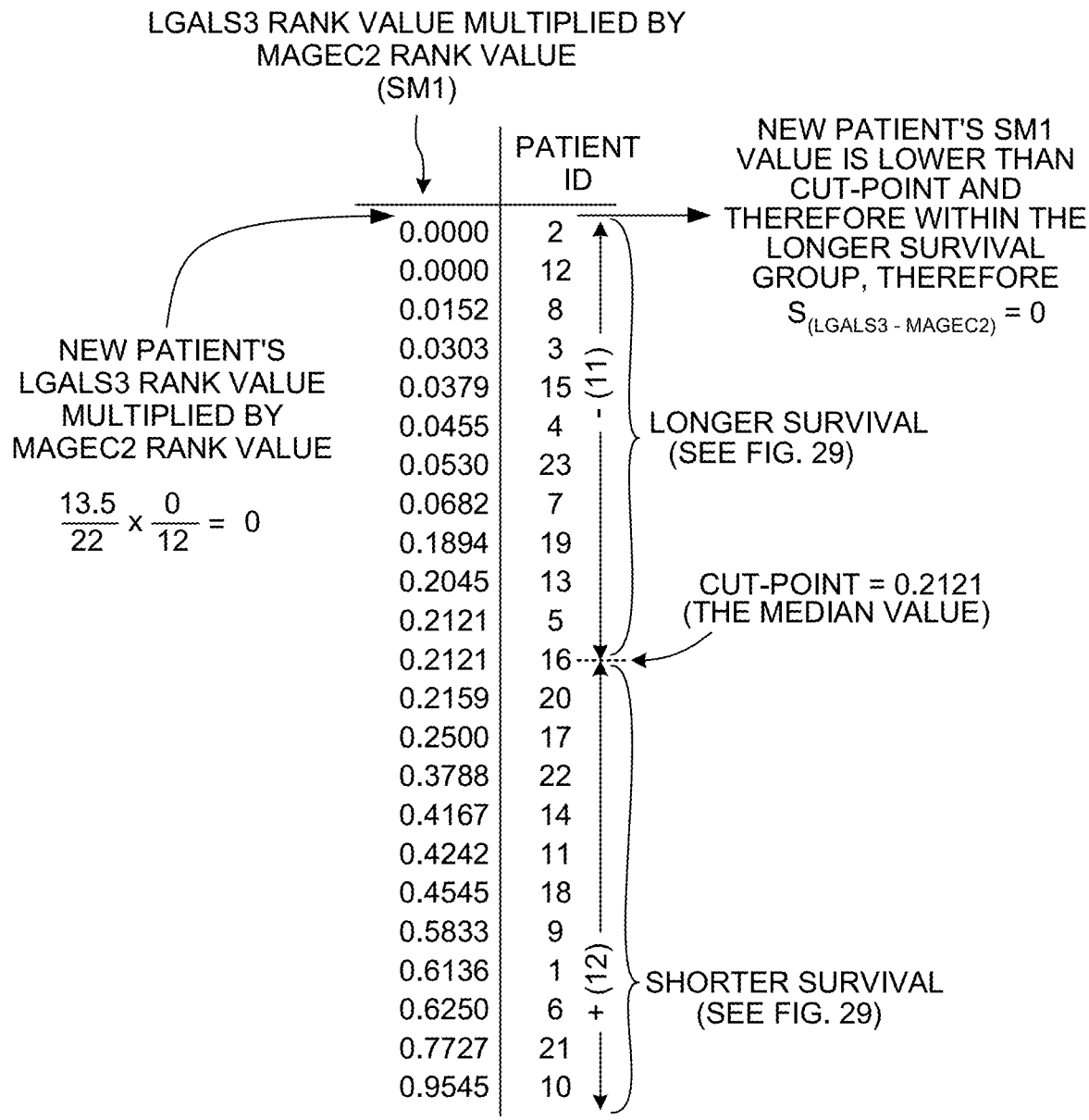
FIG. 40 shows how a score value is determined in the diagnostic phase for the LGALS3-to-MAGEC2 bivariate feature.

FIG. 40 shows how a LGALS3-to-MAGEC2 bivariate feature score value for the new patient is determined. Because the SM1 scoring method was determined in the diagnostic phase to the scoring method for the LGALS3-to-MAGEC2 bivariate relationship that results in the lowest p-value, the SM1 scoring method is used. The rank normalized list of rank values of FIG. 24 for the SM1 scoring method is replicated in FIG. 40. The rank value for the new patient is determined using the 13.5/22 rank value for LGALS3 as determined in connection with FIG. 37 and the 0/12 rank value for MAGEC2 as determined in connection with FIG. 38. As illustrated in FIG. 40, the SM1 equation is applied to these two rank values, resulting in a SM1 rank value for the LGALS3-to-MAGEC2 bivariate relationship of 0.0000. As can be seen from FIG. 40, this 0.0000 rank value is located at the top of the ordered list of rank values of FIG. 40. In the ordered list of FIG. 40, rank values that are smaller than the 0.2121 cut-point value are associated with the longer survival group of patients, and rank values that are larger than the 0.2121 cut-point value are associated with the shorter survival group of patients. Because the LGALS3-to-MAGEC2 SM1 value of 0.0000 is smaller than the 0.2121 cut-point value, it is within the longer survival group of patients, and the $S_{(LGALS3-MAGEC2)}$ score value is determined to be "0".

Figure 41:
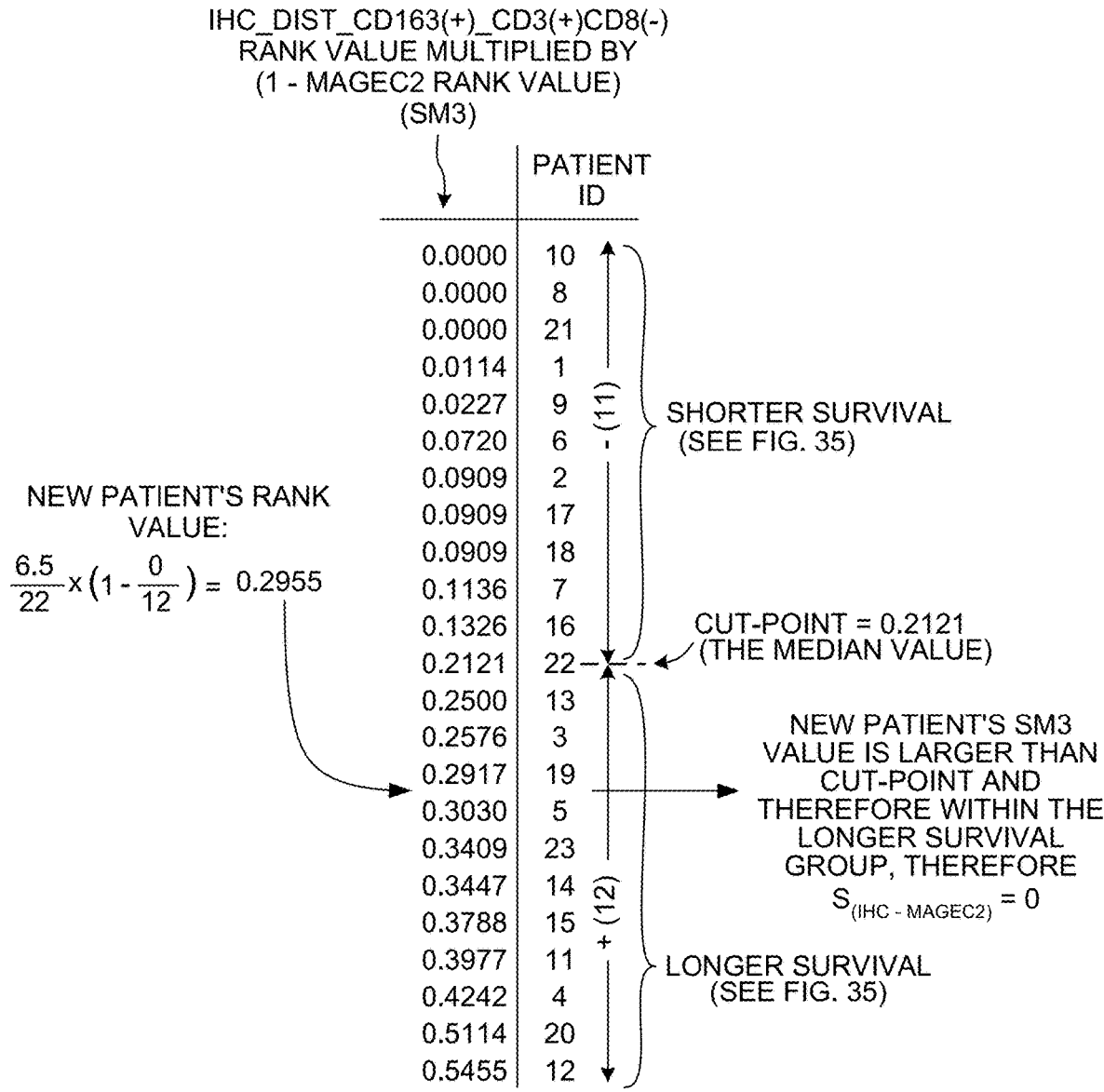
FIG. 41 shows how a score value is determined in the diagnostic phase for the IHC_DIST_CD163(+)_CD3(+) CD8(−)-to-MAGEC2 bivariate feature.

FIG. 41 shows how a IHC_Dist_CD163(+)_CD3(+)CD8(−)-to-MAGEC2 bivariate feature score value for the new patient is determined. The same process described above in connection with FIG. 40 is used. Because the SM3 scoring method was determined in the diagnostic phase (see FIG. 34) to be the scoring method having the smallest p-value, the SM3 scoring method is used. The list of rank values of FIG. 32 for the SM3 scoring method is replicated in FIG. 41. Rank values that are smaller than the cut-point value of 0.2121 are for patients in the shorter survival group of patients, whereas rank values that are larger than the cut-point value of 0.2121 are for patients in the longer survival group of patients. The rank value for the new patient is determined using the IHC rank value of 6.5/22 (see FIG. 39) and the MAGEC2 rank value of 0/12 (see FIG. 38). The SM3 equation is applied to these two rank values, resulting in an SM3 rank value for the bivariate relationship of 0.2955. As can be seen from FIG. 41, this 0.2955 rank value is located between the rank value for patient number 9 and the rank value for patient number 6. Because the 0.2955 rank for the new patient is larger than the 0.2121 cut-point value, it is within the longer survival group of patients. The $S_{(IHC-MAGEC2)}$ score value is therefore determined to be "0".

The score 2 generated by the system 1 of FIG. 1 for the new patient is a function of the three univariate feature score values $S_{LGALS3}$, $S_{MAGEC2}$ and $S_{IHC}$, and of the two bivariate feature score values $S_{(LGALS3-MAGEC2)}$ and $S_{(IHC-MAGEC2)}$. In the present example, this function is a majority voting function (see FIG. 42). Each of the five feature score values is a number which is either 0 or 1. The five feature score values are summed, and if the sum is greater than 2.5 then the overall score (the score 2 of FIG. 1) is determined to be "1", otherwise the overall score (the score 2 of FIG. 1) is determined to be "0". An overall score of "0" indicates that cancer recurrence is determined to be unlikely. An overall score of "1" indicates that cancer recurrence is determined to be likely.

FIG. 43 shows how the function of FIG. 42 is applied in the case of the new patient whose score 2 is being determined. The sum of the five features score values is 2, and this sum is smaller than 2.5, so score 2 as determined by the system 1 of FIG. 1 is "0". This score value of "0" is displayed on the display 9 of the computer 7 of FIG. 1. In the example of FIG. 2, three windows 48, 49 and 50 are presented on the display 9. The extended MST 13 is rendered in window 48. Text stating "SCORE=0" is rendered in window 49. A graphical user interface visualization element 51 is rendered in window 50.

FIG. 44 is a diagram that shows the graphical user interface visualization element 51 in further detail. The visualization element 51 visualizes PSA recurrence risk of the new patient with an arrow 54. The visualization is presented in the context of the bivariate feature IHC_DST_CD163(+)_CD3(+)CD8(−)-to-MAGEC2 (IHC_DST_CD163(+)_CD3(+)CD8(−) and not MAGEC2). Box 52 depicts the rank values of the twelve learning phase patients whose rank values appear below the cut-point value in FIG. 41, whereas box 53 depicts the rank values of the eleven learning phase patients whose rank values appear above the cut-point value in FIG. 41. The textual note "IHC and not MAGEC2" 55 is a graphical indication of the scoring method of the bivariate feature, which in this case is scoring method SM3. The user of the system 1 of FIG. 1 can view the extended MST 13 on display 9 of the computer 7, and then use the computer's mouse or other pointing tool to select a feature of the extended MST. This selected feature may, for example, be the bivariate prognostic feature mentioned above. As a result of this selection, the system causes the diagram of FIG. 44 to be presented to the user in window 50 at the same time that the extended MST is presented in the window 48. The diagram in window 50 provides more detailed underlying data about the selected feature that is shown at a higher level of abstraction (as a node or edge) in the extended MST 13.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method for providing a graphical indication of whether a patient will have a recurrence of prostate cancer, comprising:
   (a) measuring a first feature to obtain a first value based on an object detected in a digital image of a first tissue slice that has been stained with a protein-specific immunohistochemical (IHC) biomarker, wherein the first tissue slice was cut from a formalin fixed paraffin embedded (FFPE) tissue sample of prostate cancer from the patient, wherein the first feature is a univariate prognostic feature for the recurrence of prostate cancer in a cohort of patients exhibiting prostate cancer, and wherein the univariate prognostic feature is taken from the group consisting of: IHC DIST CD163(+) CD8(+) STROMA, IHC DIST CD34(+) CD163(+) STROMA, IHC DIST CD163(+) CD3(+)CD8(−), CD59, MAGEC2, ATF2, NFKBIA, CXCL13, NUP107, IL12A, JAK2, SYCP1, MAPK1, TBX21, SYK, ANXA1, PMCH, MBL2, C4B, BMI1, CCL5, STAT4, IRF1, CD47, PSEN2, CD96, CTSH, IL17B, DDX43, KLRK1, LGALS3, and PTGDR2;
   (b) measuring a second feature to obtain a second value based on objects marked with an mRNA-specific probe biomarker detected in a second tissue slice that was cut from the FFPE tissue sample, wherein a combination of the first feature and the second feature is a bivariate prognostic feature for the recurrence of prostate cancer in the cohort, wherein the first feature and the second feature are elements of a minimal spanning tree that is constructed from univariate and bivariate prognostic features for the recurrence of prostate cancer in the cohort, wherein nodes of the minimal spanning tree represent the univariate prognostic features, wherein edges of the minimal spanning tree represent the bivariate prognostic features, and wherein weights of the edges represent prognostic significance of the bivariate prognostic features; and
   (c) displaying the graphical indication of the combination of the first value and the second value on a graphical user interface to illustrate whether the patient will have a recurrence of prostate cancer.

2. The method of claim 1, wherein the minimal spanning tree is generated by Prim's algorithm, and the edge weights are related to a Kaplan Meier log rank p value of the bivariate prognostic features in the cohort.

3. The method of claim 1, wherein the bivariate prognostic feature is generated by a combination of two features f1 and f2 using a formula taken from the group consisting of: f1×f2 and (1-f1)×f2 and f1×(1-f2) and (1-f1)×(1-f2).

4. The method of claim 1, further comprising:
   generating the bivariate prognostic feature by combining normalized rankings of the first feature and the second feature according to how the patients in the cohort exhibited the recurrence of prostate cancer.

5. The method of claim 1, wherein the graphical indication illustrates a risk of prostate cancer recurrence for an individual patient based on statistics of the risks of the cohort of patients.

6. A system for providing a graphical indication of whether a patient will have a recurrence of prostate cancer, comprising:
   (a) code for measuring a first feature to obtain a first value based on an object detected in a digital image of a first tissue slice that has been stained with a protein-specific immunohistochemical (IHC) biomarker, wherein the first tissue slice was cut from a formalin fixed paraffin embedded (FFPE) tissue sample of prostate cancer from the patient;
   (b) code for measuring a second feature to obtain a second value based on objects marked with an mRNA-specific probe biomarker detected in a second tissue slice that was cut from the FFPE tissue sample, wherein the first feature is a univariate prognostic feature for the recurrence of prostate cancer in a cohort of patients exhibiting prostate cancer, wherein a combination of the first feature and the second feature is a bivariate prognostic feature for the recurrence of prostate cancer in the cohort, wherein the first feature and the second feature are elements of a minimal spanning tree that is constructed from univariate and bivariate prognostic features for the recurrence of prostate cancer in the cohort, wherein nodes of the minimal spanning tree represent the univariate prognostic features, wherein edges of the minimal spanning tree represent the bivariate prognostic features, and wherein weights of the edges represent prognostic significance of the bivariate prognostic features, and wherein the univariate prognostic feature is taken from the group consisting of: IHC DIST CD163 (+) CD8(+) STROMA, IHC DIST CD34(+) CD163(+) STROMA, IHC DIST CD163(+) CD3(+)CD8(−), CD59, MAGEC2, ATF2, NFKBIA, CXCL13, NUP107, IL12A, JAK2, SYCP1, MAPK1, TBX21, SYK, ANXA1, PMCH, MBL2, C4B, BMI1, CCL5, STAT4, IRF1, CD47, PSEN2, CD96, CTSH, IL17B, DDX43, KLRK1, LGALS3, and PTGDR2; and
   (d) a graphical user interface that displays the graphical indication of the combination of the first value and the second value so as to illustrate whether the patient will have a recurrence of prostate cancer.

7. The system of claim 6, wherein the minimal spanning tree is generated by Prim's algorithm, and the edge weights are related to a Kaplan Meier log rank p value of the bivariate prognostic features in the cohort.

8. The system of claim 6, wherein the bivariate prognostic feature is generated by a combination of two features f1 and f2 using a formula taken from the group consisting of: f1×f2 and (1-f1)×f2 and f1×(1-f2) and (1-f1)×(1-f2).

9. The system of claim 6, wherein the bivariate prognostic feature is generated by combining a normalized ranking of the first feature with a normalized ranking of the second feature according to how the recurrence of prostate cancer is exhibited in the cohort of patients.

10. The system of claim 6, wherein the graphical indication illustrates a risk of prostate cancer recurrence for an individual patient based on statistics of the risks of the cohort of patients.

11. The system of claim 6, wherein the graphical indication of the combination of the first value and the second value is an indication of whether measurable prostate-specific antigen (PSA) will be present in the future in blood of the patient.

12. The system of claim 6, wherein the combination of the first value and the second value are indicative of whether there will be a recurrence of measurable prostate-specific antigen (PSA) in blood of the patient.

13. A method of using both phenomic features and genomic features to indicate whether a patient will have a recurrence of a cancer, comprising:
   (a) measuring a phenomic feature to obtain a first value based on an object detected in a digital image of a first tissue slice that has been stained with a protein-specific immunohistochemical (IHC) biomarker, wherein the first tissue slice was cut from a formalin fixed paraffin embedded (FFPE) tissue sample of the cancer from the patient, wherein the phenomic feature is empirically determined to be indicative of the recurrence of the cancer in a cohort of patients exhibiting the cancer, and wherein the phenomic feature is a univariate prognostic feature taken from the group consisting of: IHC DIST CD163(+) CD8(+) STROMA, IHC DIST CD34(+) CD163(+) STROMA, IHC DIST CD163(+) CD3(+) CD8(−), CD59, MAGEC2, ATF2, NFKBIA, CXCL13, NUP107, IL12A, JAK2, SYCP1, MAPK1, TBX21, SYK, ANXA1, PMCH, MBL2, C4B, BMI1, CCL5, STAT4, IRF1, CD47, PSEN2, CD96, CTSH, IL17B, DDX43, KLRK1, LGALS3, and PTGDR2;
   (b) measuring a genomic feature to obtain a second value based on objects marked with an mRNA-specific probe biomarker detected in a second tissue slice that was cut from the FFPE tissue sample, wherein the genomic feature is empirically determined to be indicative of the recurrence of the cancer in the cohort of patients exhibiting the cancer, wherein a combination of the phenomic feature and the genomic feature is a combination feature for the recurrence of the cancer in the cohort, wherein a minimal spanning tree is constructed from phenomic features and combination features for the recurrence of the cancer in the cohort, wherein nodes of the minimal spanning tree represent the phenomic features, wherein edges of the minimal spanning tree represent the combination features, and wherein weights of the edges represent prognostic significance of the combination features; and
   (c) displaying a graphical indication of the phenomic feature and the combination feature on a graphical user interface to illustrate whether the patient will have a recurrence of the cancer.

14. The method of claim 13, further comprising:
generating the combination feature by combining normalized rankings of the phenomic feature and the genomic feature according to how the patients in the cohort exhibited the recurrence of the cancer.

* * * * *